United States Patent
Reydel et al.

(10) Patent No.: US 7,967,798 B2
(45) Date of Patent: Jun. 28, 2011

(54) INTRODUCER APPARATUS WITH EVERSIBLE SLEEVE

(75) Inventors: Boris Reydel, Passaic, NJ (US); Mikhail Mezhirov, Bridgeport, CT (US); Jason D. Foushee, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 870 days.

(21) Appl. No.: 10/692,310

(22) Filed: Oct. 22, 2003

(65) Prior Publication Data

US 2006/0173422 A1    Aug. 3, 2006

Related U.S. Application Data

(63) Continuation of application No. 09/847,494, filed on May 2, 2001, now abandoned.

(60) Provisional application No. 60/201,116, filed on May 2, 2000.

(51) Int. Cl.
*A61M 5/00* (2006.01)
*A61F 11/00* (2006.01)

(52) U.S. Cl. ........................... 604/271; 606/108

(58) Field of Classification Search .......... 606/108, 606/149; 604/171, 271, 172, 264, 265, 508, 604/510, 523, 528; 600/581, 585
See application file for complete search history.

(56) References Cited

U.S. PATENT DOCUMENTS

| | | | |
|---|---|---|---|
| 3,421,509 A | 1/1969 | Fiore | |
| 3,583,391 A * | 6/1971 | Cox et al. ................ | 600/585 |
| 3,595,230 A | 7/1971 | Suyeoka et al. | |
| 4,077,610 A | 3/1978 | Masuda | |
| 4,321,915 A | 3/1982 | Leighton et al. | |
| 4,479,497 A * | 10/1984 | Fogarty et al. ............ | 606/194 |
| 4,540,409 A | 9/1985 | Nystrom et al. | |
| 4,586,974 A | 5/1986 | Nystrom et al. | |
| 4,604,094 A | 8/1986 | Shook | |

(Continued)

OTHER PUBLICATIONS

Alspaugh et al., "Everting Balloon Catheter in the Biliary Tree: A Technical Note", *CardioVascular and Interventional Radiology*, vol. 9, pp. 164-166, 1986.
Benjamin et al, "The Toposcopic Through-Lumen Everting Catheter to Facilitate Dilation of Severe Strictures of the Gastrointestinal Tract", *Gastrointestinal Endoscopy*, vol. 32, No. 1, pp. 33-35, 1986.
Goldstein et al., "The Toposcopic Catheter and the Fiberoptic pH Probe-Two Medical Instrucments of Potential Use to Gastroenterologist", *Endoscopy*, vol. 29, No. 3, pp. 236-240, 1983.

(Continued)

*Primary Examiner* — Theodore J Stigell
*Assistant Examiner* — Catherine N Witczak
(74) *Attorney, Agent, or Firm* — Brinks Hofer Gilson & Lione

(57) ABSTRACT

Disclosed is an introducer apparatus comprising an sleeve fixation mechanism or introducer member, such as a catheter, introducer, or ring-like structure, which is attached to a protective sleeve comprising a thin flexible material such a polymeric film. The sleeve is inverted into the passageway of a second member, such as a catheter, feeding tube, introducer, etc., that is advanced through the passageway of the introducer member and is introduced into a bodily passage of a patient, such as the bile duct, nasal passages, colon, etc. The sleeve everts from the passageway of the second member during its advancement to lay down a friction-reducing surface. The sleeve prevents frictional contact between the second member and delicate or sensitive tissues.

41 Claims, 10 Drawing Sheets

U.S. PATENT DOCUMENTS

| | | | |
|---|---|---|---|
| 4,946,440 A * | 8/1990 | Hall | 604/164.09 |
| 5,171,305 A | 12/1992 | Schickling et al. | |
| 5,236,423 A | 8/1993 | Mix et al. | |
| 5,364,345 A | 11/1994 | Lowery et al. | |
| 5,389,089 A * | 2/1995 | Bauer et al. | 604/271 |
| 5,423,784 A | 6/1995 | Metz | |
| 5,458,573 A | 10/1995 | Summers | |
| 5,538,584 A | 7/1996 | Metz | |
| 5,567,283 A | 10/1996 | Green et al. | |
| 5,779,670 A | 7/1998 | Bidwell et al. | |
| 5,792,114 A | 8/1998 | Fiore | |
| 6,007,521 A | 12/1999 | Bidwell et al. | |
| 6,039,721 A | 3/2000 | Johnson et al. | |
| 6,217,569 B1 | 4/2001 | Fiore | |

OTHER PUBLICATIONS

Reydel et al., U.S. Appl. No. 09/847,494, filed May 2, 2001, now abandoned.

Shook et al., "Everting (Toposcopic) Catheter for Broad Clinical Application", *Transactions of the ASME*, vol. 108, pp. 168-174, 1986.

Shook, D.R., "The Ins and Outs of Toposcopy and the Everting Catheter", *SOMA*, pp. 22-27, 1987.

* cited by examiner

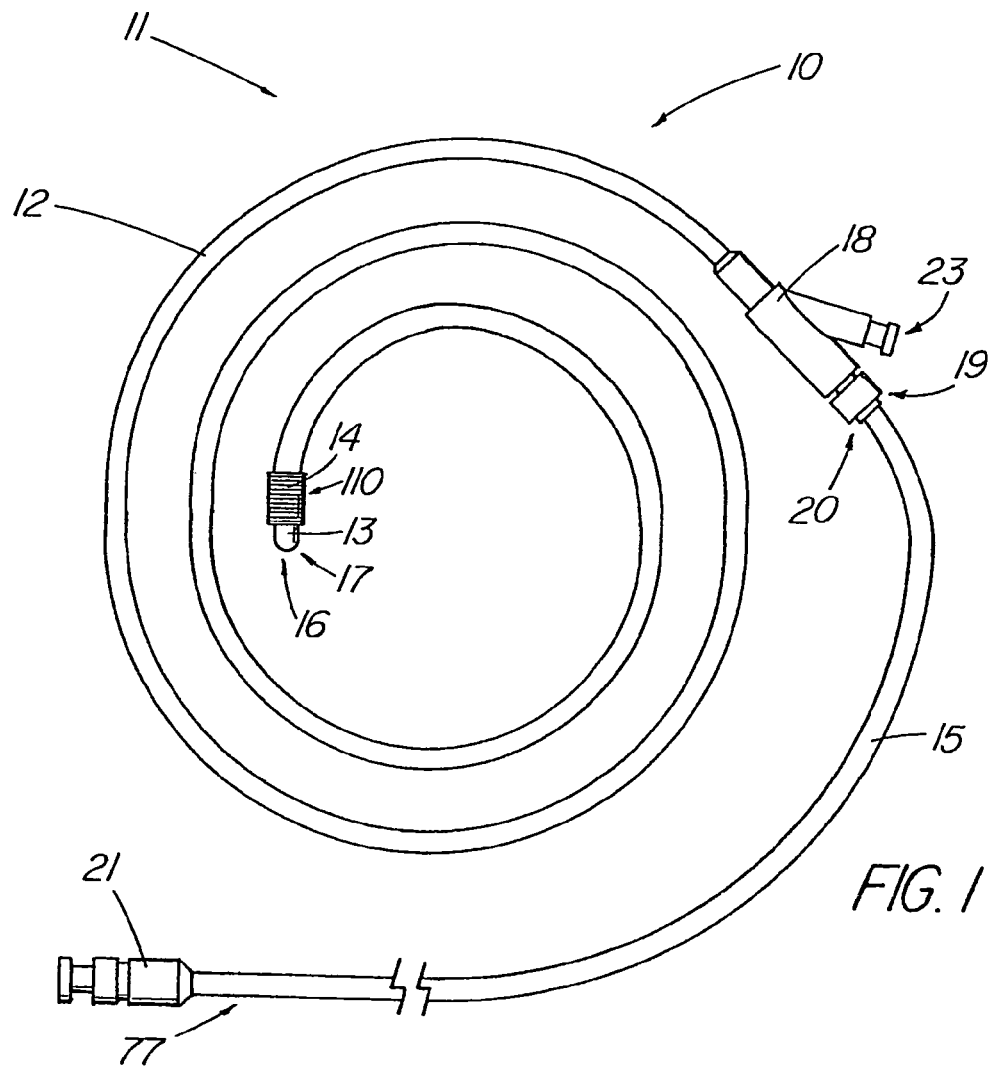
FIG. 1
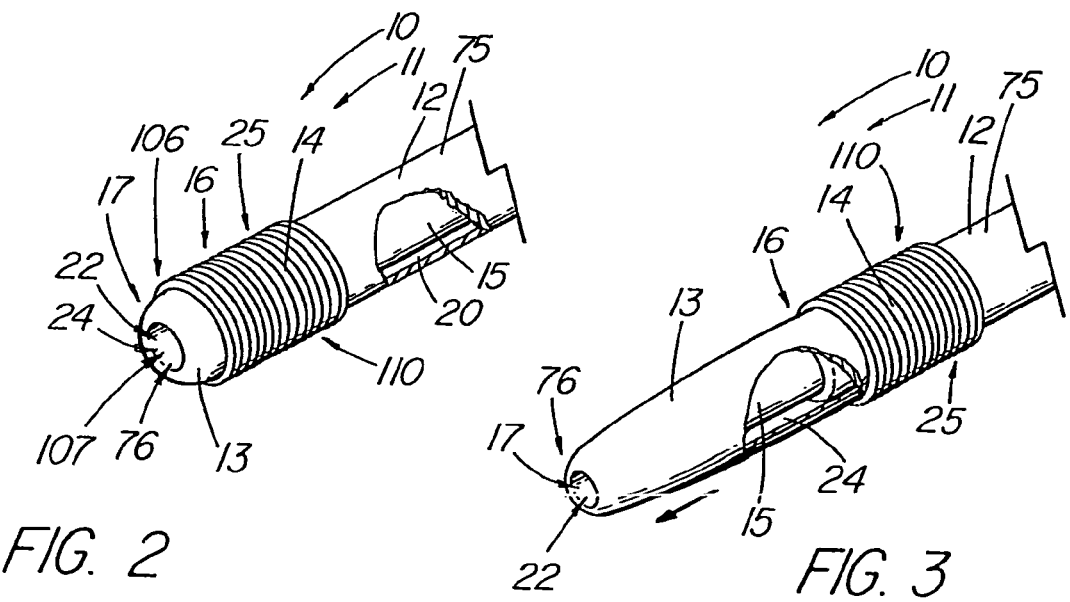
FIG. 2
FIG. 3

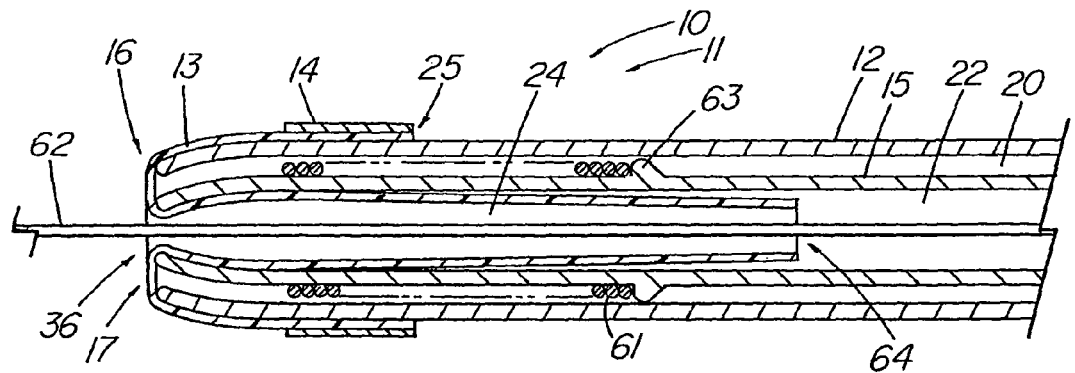
FIG. 20
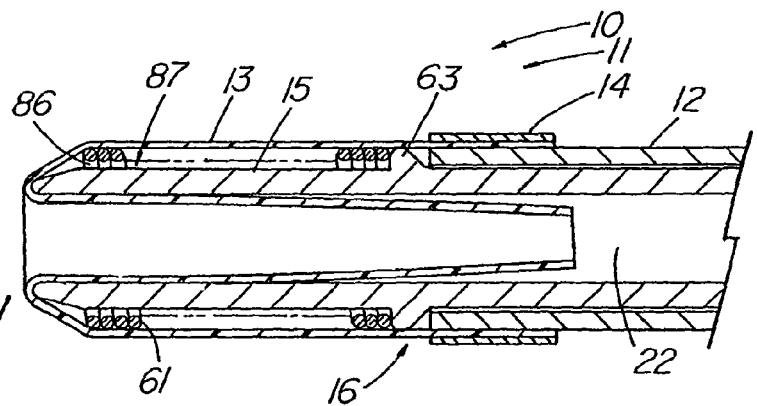
FIG. 21
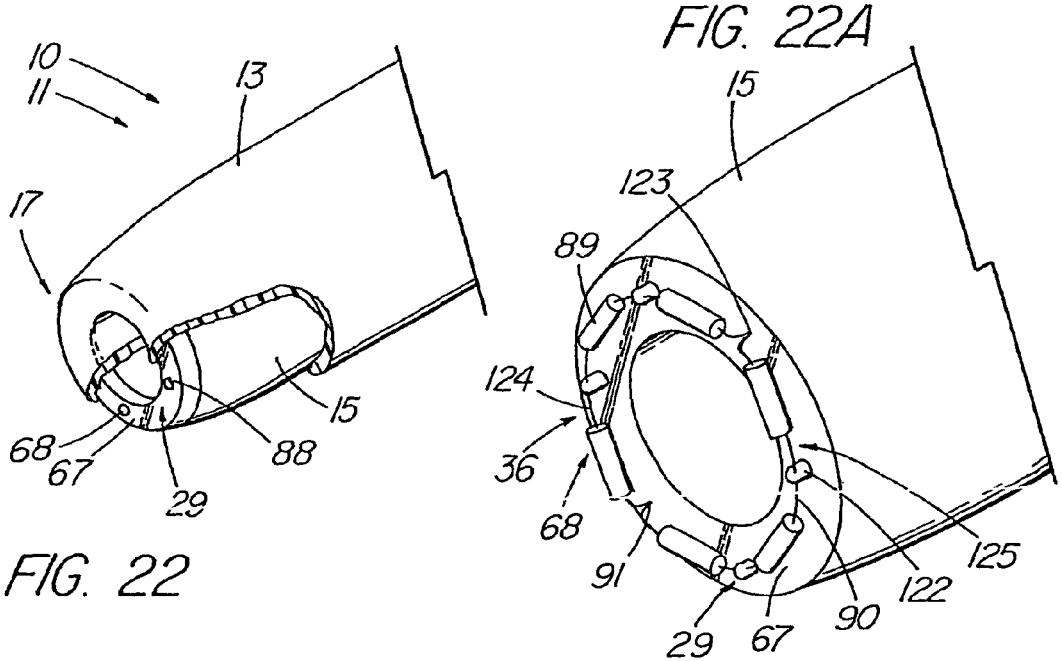
FIG. 22
FIG. 22A

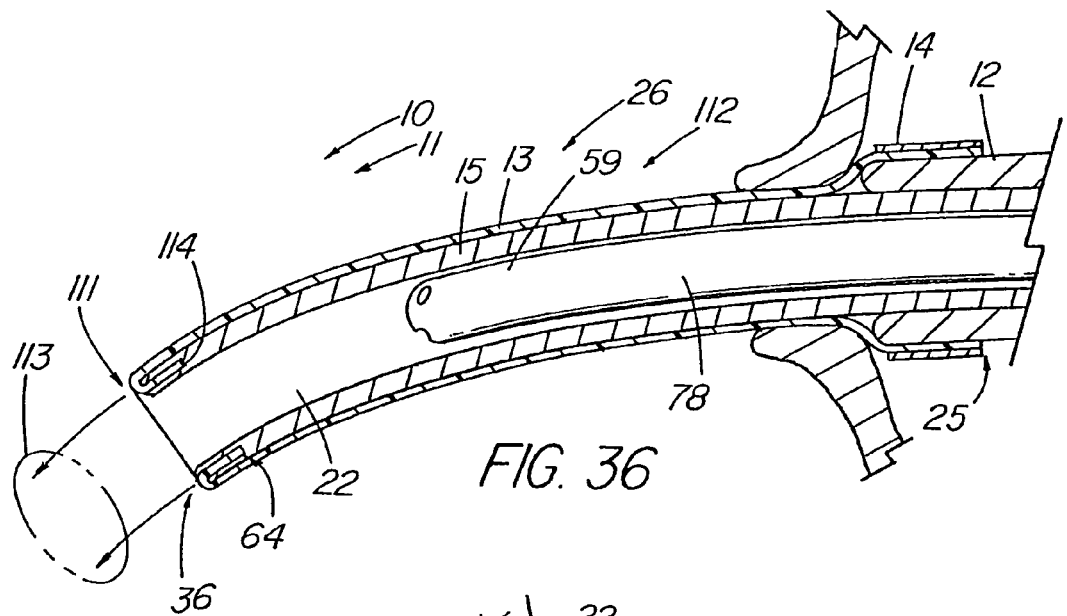
FIG. 36
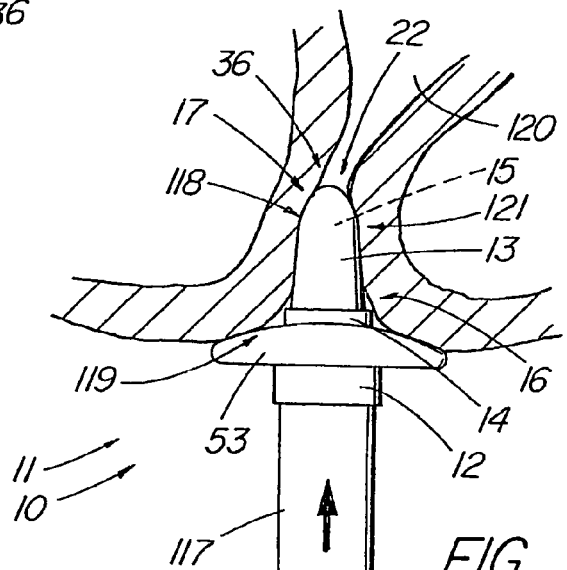
FIG. 37
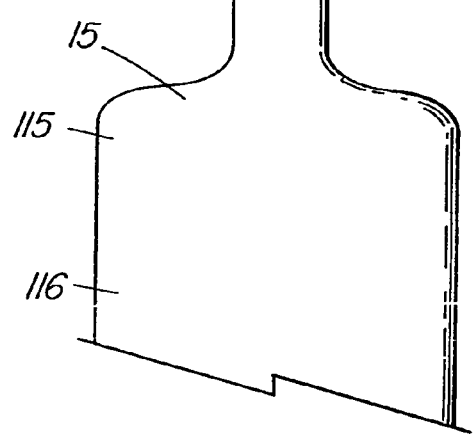

INTRODUCER APPARATUS WITH EVERSIBLE SLEEVE

CROSS-REFERENCE TO RELATED APPLICATIONS

This application is a continuation of U.S. patent application Ser. No. 09/847,494, filed May 2, 2001 now abandoned, which claims priority to U.S. Provisional Application Ser. No. 60/201,116 filed May 2, 2000.

TECHNICAL FIELD

This invention relates to medical devices, more particularly to catheters introduced into body lumens.

BACKGROUND OF THE INVENTION

Despite the efforts of medical device manufacturers to reduce the coefficient of friction for their catheters, especially those intended for introduction through a sphincter or narrow body lumen, there is very often a problem with discomfort to the patient or trauma to delicate or sensitive tissues as the catheter is being advanced. Lubricants and lubricious polymers or other coatings can reduce these effects, but not always to a sufficient degree. In the biliary system, for example, passing a biliary catheter through the Papilla of Vater and into the common bile duct very often results in swelling and subsequent closure of the opening, compromising normal drainage and making subsequent access difficult. Similar problems with discomfort or edema can be experienced by the patients when other anatomical sites are being accessed, for example, in the nasal passages, urethra, rectum, etc. While patient comfort may not be an issue when navigating internally such as within the biliary tree, the introduced device may be difficult or even impossible to advance from frictional forces acting against it, especially since these obstructions and narrowed passages often cannot be adequately visualized.

One approach to reduce patient discomfort when introducing a catheter or similar device, is to include a sheath or sleeve which is laid down by the advancing device to prevent frictional contact between the device and the delicate lining of the bodily passage. A urethral catheter with an outer sleeve is disclosed in U.S. Pat. No. 5,779,670 to Bidwell in which the latex sleeve is fixedly and sealingly attached to the inside of the catheter by a sliding retention sled and to the outside of the catheter by a slidable collar. The sleeve allows relative movement of the catheter to the urethra without the normal friction that causes patient discomfort during introduction and wearing of the device. A lubricant fills the space created between the sleeve and the catheter which is intended to further reduce friction between the two surfaces. While the '670 concept may be suitable to traverse the urethra for purposes of draining the bladder, it is not useful for other anatomical sites and procedures in which having the sleeve attached to the inside of the catheter is not desired, such as in an ERCP (Endoscopic Retrograde Cholangiopancreatography) procedure or placement of a nasal-jejunal feeding tube or colonic decompression catheter. In these procedures, the sleeve might be used advantageously in combination with the introduced device to access a narrow duct or opening, to cannulate a stricture, or navigate over folds of tissue, but its eventual removal from the inner member passageway is typically required to complete the procedure. In the case of a feeding or decompression tube, continued presence of the sleeve over the catheter would block critical side holes. For these reasons, the Bidwell concept is not suitable for the introduction of a second medical device into the body.

Besides the biliary system, other sites within the body present an opportunity for improved patient comfort and reduced trauma by the reduction of friction during the introduction of a device. For example, the nasal passages are especially sensitive and recent trends have brought about an increase in the number of devices, such as endoscopes and tubes, being introduced via that route concomitant with the use of analgesics or sedatives to reduce patient discomfort. Another situation where reduction of friction would be important is in the lower gastrointestinal tract where folds within the colon can provide sufficient resistance to an introduced catheter or other device where in many cases, the tip of the catheter bends back on itself, rather than continuing to advance to the treatment site. Therefore, what is needed is a friction-reducing introducer apparatus that can be used with a separate catheter, sheath, or other medical devices to permit the safe and comfortable passageway thereof into and/or through a bodily passage, and is removable from the treatment site so as not to possibly interfere with the function of the introduced device(s).

SUMMARY OF THE INVENTION

The foregoing problems are solved and a technical advance is achieved in an apparatus for introducing a second medical device, such as an inner member or an elongated member, into a bodily passage, the introducer apparatus comprising a sleeve fixation mechanism, such as an introducer member. The sleeve fixation mechanism facilitates engagement of the sleeve with the opening of the bodily passage and can include a variety of structures, such as an introducer sheath, tube, ring-like member, barbs, or other structure which is permanently or releasably attached to a full or partial sleeve which is made of a thin, flexible material. The sleeve, which can be made of variety of biocompatible materials such as expanded polytetrafluoroethylene (ePTFE) or polyethylene film, is sufficiently flexible to be made eversible or such that one end can be inverted back through the passageway of an introducer member and loaded into the passageway of a second member, such as a catheter, that functions as a coaxial inner member and also serves as the medical device being introduced into the bodily passage. The inverted sleeve is then pulled from the inner member passageway and laid down within the bodily passage or the opening thereto by the inner member as it advances out of or through the introducer member, which is typically maintained in a nearly stationary position and generally does not enter the target bodily passage, although, such as in the case of a biliary catheter, may be introduced through other body lumens to position the inner member at the opening to a remote bodily passage.

As a result of the cooperation between the sleeve, the introducer member, and the inner member, neither the sleeve nor the inner member frictionally slides against the bodily passage during advancement, thereby providing improved patient comfort and/or facilitating forward movement which may reduce trauma to the sphincter, duct or body lumen through which it is being introduced. In addition to reducing friction, the sleeve can act to provide a smooth track over an uneven surface, such as the tissue folds that occur within the Papilla of Vater or the intestinal tract. The sleeve is designed to be completely or functionally eversible at full deployment from the inner member passageway (maximum extension of the inner member relative to the sleeve), such that the passageway of the inner member can be at least substantially cleared and be functionally unobstructed. Typically, but not essentially, the second end of the sleeve is unattached to the inner member; however, if it attached, it has the ability to substantially clear the passageway such that the sleeve or attachment does not interfere with the passage of devices or materials through the inner member. Partial deployment of the inner member, which may also be desired in some applications, can result in a portion of the sleeve still remaining in the inner member passageway. In addition to making it simpler and cheaper to manufacture, leaving the second end unattached, makes it easier to remove the introducer assembly from the patient while maintaining the inner member in place. Additionally, it allows the passageway of the inner member to be free of obstructions and have a maximum possible diameter for passage of other devices, once the sleeve has completely everted. Alternatively, the sleeve may also be attached to the inner member in a manner, such as around the distal tip, that the sleeve can evert out of the passageway to a sufficient degree as not to interfere with the passage of a third medical device, such as a endoscope, through the inner member conduit. Attachment of the sleeve, while substantially maintaining the patency of the passageway, would be functionally equivalent to having an unattached and fully-eversible sleeve, and thus, fall within the scope of the present invention.

In another aspect of the present invention, the introducer apparatus is adapted to permit the inner member to laterally deflect as it advances from the introducer member and causes the sleeve to evert. This can be accomplished by the addition of an asymmetrical tip to the inner member or making the inner member itself asymmetrical such that the sleeve has more drag on one side, thereby causing the inner member to deflect in that direction. This property is advantageous in certain clinical situations such as in the biliary tree where there is a bifurcation between the bile and pancreatic ducts. Another means of causing the inner member to deflect in a given direction is to modify the sleeve such that one side has a greater coefficient of friction than the other. This can be accomplished by removing a portion of sleeve longitudinally to make a half sleeve, making the sleeve out of two materials, or treating one half of the sleeve such that the half having a greater coefficient of friction causes the inner member to bend in that direction as it advances through the bodily passage.

In still another aspect of the present invention, the introducer member and sleeve are made splittable with a predetermined split line such that they can be removed from over the inner member within the patient, without requiring its removal or causing its dislodgement. Other methods of removing the introducer member from the inner member include making the inner member twice as long as the outer so that is can be removed from the patient and left over the external portion of the indwelling inner member, or having a removable/replaceable connector on the inner member so that the introducer member can be removed over the proximal end of the inner member.

In yet another aspect of the present invention, a tether is affixed to the second (inverted) end of the sleeve for reloading the sleeve once it has partially everted. The attachment may be such that the sleeve passageway is maintained in an open state to facilitate access by other medical devices, such as a wire guide, being introduced therethrough. This can include a reinforcing annular ring within or external to the second end of the sleeve and/or a second tether.

In still yet another aspect of the present invention, the introducer apparatus can include means for reducing friction between the sleeve and inner member during its use. One embodiment includes folding or pleating the sleeve to shorten it within the passageway and reduce the amount of contact with the inside of the inner member passageway. This pleated sleeve unfolds as it is everted by the advancing inner member. Another method is to modify the distal end of the inner member to reduce friction. Besides changing the surface energy of the tip, including adding a second more lubricious material, the tip can be made to ease frictional movement of the sleeve by the addition of ball bearings or rollers to the tip which rotate as the sleeve is passed thereover.

In still yet another aspect of the present invention, the introducer member comprises a short annular ring or collar that is slidable over the inner member that is being introduced therethrough, rather than an elongated introducer catheter. This embodiment has utility when directly accessing the target bodily passages from outside the body such as when placing nasal-gastric or nasal-jejunal feeding tubes, colonic decompression catheters, and urethral catheters, etc. In these types of procedures, the operator can grasp the outer ring directly adjacent the introduction site and deploy the inner member, rather than to first navigate the introducer apparatus to a remote location in the body, such as the Papilla of Vater and common bile duct. The outer ring can also be provided by forming a thickened portion of the sleeve material at or near the first end of the sleeve.

In still yet another aspect of the present invention, either the introducer member or second member can include additional lumens for passage of other devices or injection of materials such as contrast agents with one passageway receiving the eversible sleeve and at least one other adjacent passageway remaining free to serve a different function. Contrast media, as well as other agents, can also be introduced through the sleeve itself via a plurality of apertures in the material, such as a mesh.

In still yet another aspect of the present invention, the introducer apparatus can be placed over a nasal-gastric (NG) tube, or other medical device such that the inner member comprises a cap-like structure with the sleeve everting from within the lumen of the inner member which frictionally protects the bodily passage from the NG tube and advancing inner member. The sleeve everts from a distal chamber in the inner member which is separated by a proximal receiving chamber housing the distal end of the NG tube by a partial septum. The introducer member ring is tethered to the inner member for pulling the inner member proximally over the inner NG tube, allowing the latter to advance through the partial septum and out of the inner member for final placement.

In still yet another aspect of the present invention, the inner member of the introducer apparatus is made radially expandable such that once it is introduced into the body, e.g., the back of the throat for placement of an NG tube, the sleeve is removed and a larger device (the NG tube) can be introduced therethrough as the inner member expands to accommodate its passageway. Embodiments of this concept include having the inner member comprise a cut, rolled tube with overlapping edges that allow for its expansion, and an inner member having a folded pleat on one or more sides that permits limited expansion of the introducer during passage of a device such as an NG tube.

In still yet another aspect of the present invention, the inner member includes a fluid reservoir, such as a bottle for delivery of an enema. The outer member comprises a ring-like structure that slides over the neck of the bottle, the neck utilizing the eversible sleeve to reduce patient discomfort when traversing the anal sphincter as the outer member ring abuts the peri-anal area.

BRIEF DESCRIPTION OF THE DRAWINGS

Embodiments of the present invention will now be described by way of example with reference to the accompanying drawings, in which:

FIG. 1 depicts a side view of a first embodiment of the present invention;

FIGS. 2-3 depict enlarged partially sectioned pictorial views of the embodiment of FIG. 1;

FIGS. 20-21 depicts a cross-sectional view of embodiments of the present invention used to deliver stents;

FIGS. 22-22A depict enlarged partial views of embodiments of the present invention having a reduced friction tip;

FIG. 36 depicts a partially sectioned view of an embodiment of the present invention in situ, where the sleeve is also attached about the inner member; and FIG. 37 depicts a side view of an embodiment of the present invention where the inner member comprises a fluid reservoir.

DETAILED DESCRIPTION

Figure 4:
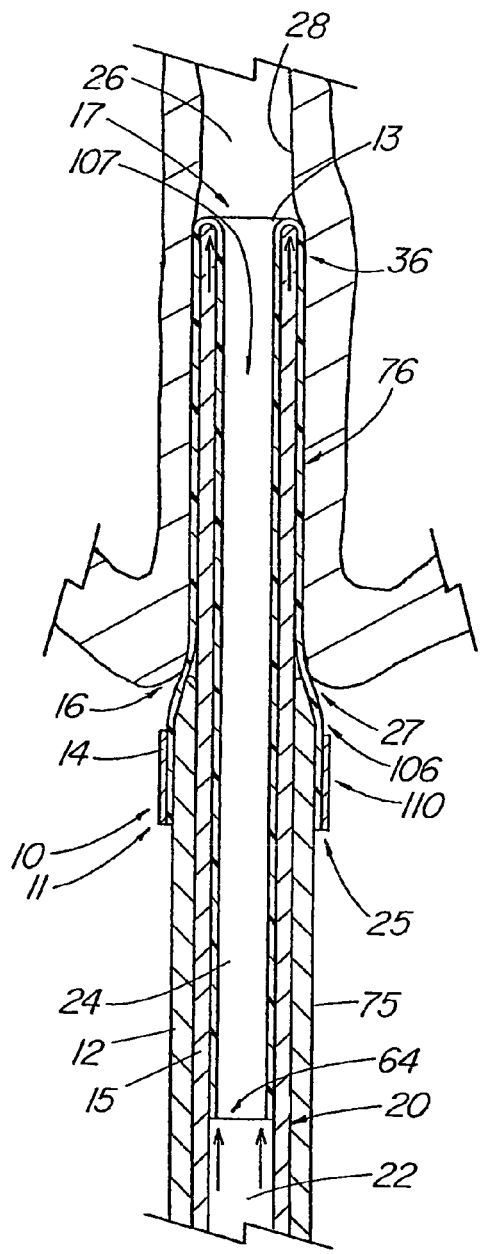
FIG. 4 depicts a cross-sectional view of the embodiment of FIG. 1 in situ.

The present invention comprises an introducer apparatus 10 for reducing friction of a medical device being introduced into a bodily passage 26, a first embodiment of which is depicted in FIGS. 1-4. The introducer apparatus 10 comprises an introducer assembly 11 that includes a sleeve fixation member 12, such as the illustrative introducer member, having a passageway 20 therethrough and a flexible sleeve 13 comprising a body 76, a first end 25 and a second end 64. The sleeve 13 also includes a first portion 106 and a second portion 107 (FIG. 4), with the first portion 106, which includes the first end 25, being attached about the introducer member by an attachment 14 which preferably, but not essentially, affixes the sleeve 13 at one or more attachment points 110 to the outer surface 75 of the introducer member 12 and is fixed against movement with respect to the introducer member 12. Although the sleeve 13 is typically attached to the introducer member 12 at the 'true' first end 25 thereof, it is possible that the sleeve 13 may also extend proximally beyond the attachment 14 such that the attachment 14 lies within what technically, could be considered the body 76 of the sleeve 13; however, functionally, the first end 25 would still occur at the point of attachment 110, especially if fixedly attached, regardless of whether unattached sleeve 13 material extended proximal to that point.

The sleeve 13 should be made of a material that allows it to be sufficiently flexible to conform to the shape of a device being placed therethrough. For most applications, the material, which is typically thin, should exhibit resistance to tearing and stretching (i.e., have good linear strength). Generally, the sleeve should be smooth and lubricious such that the sleeve, as it is laid down by the advancement of the device, or being withdrawn from the body, is atraumatic to delicate linings of the body, such as sphincters, tissue folds, ducts, and other passages. One material with particularly desirable properties is expanded polytetrafluoroethylene (ePTFE). Custom extruded ePTFE, which is available from Zeus Medical Products, Inc., Orangeburg, S.C., is produced from polytetrafluoroethylene (PTFE) tubing that is expanded under controlled conditions which advantageously adds microscopic pores throughout the material. The result is a soft, flexible material with increased linear strength. The wall thickness of the sleeve 13 depends largely on the application and material used and may typically range from 0.001-0.01" for ePTFE. A more preferred range for ePTFE when introducing a standard ERCP device would be in the 0.002-0.005" range, most preferably around 0.0025". Many other polymeric films, such as high-density or low-density polyethylene, have desirable properties, particularly those with adequate linear strength. Their lower cost can be significant, particularly for longer devices. Other possible materials include latex, woven fabrics, or biomaterials that can be fabricated into a thin, flexible sheet or tube of sufficient strength. The sleeve can also be coated or impregnated with other compounds and materials to achieve the desired properties.

Figure 18:
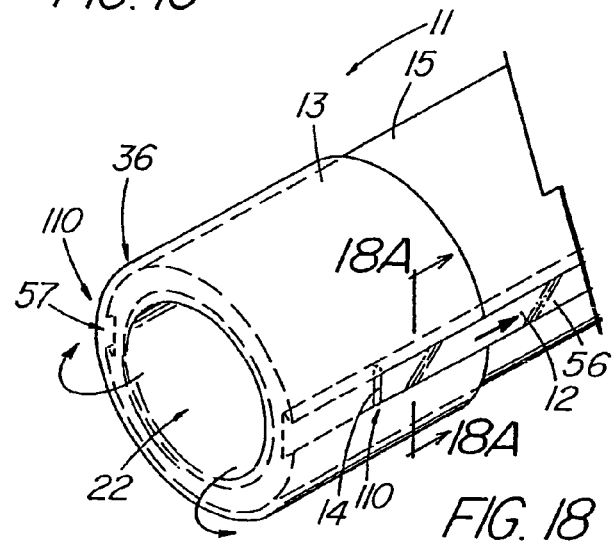
FIG. 18 depicts an enlarged pictorial view of the present invention in which the introducer member comprises attachment strips.
Figure 18A:
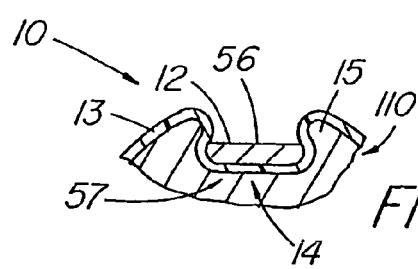
FIG. 18A depicts a partial cross-sectional view of the embodiment of FIG. 18, taken along line 18A-18A.

To achieve an attachment 14 between the sleeve 13 and introducer member 12, a variety of well-known methods can be used. Permanent bonding methods include, but are not limited to, a wrapping, such as with a thread or suture material; heat shrink wrap or tubing; thermal, laser, or ultrasonic welding; an adhesive, or a combination thereof. A detachable means of securing the sleeve can also be used, such as a ring, collar, elastic band, channel/groove, lower-grade adhesive, or another well-known means. In the illustrative embodiment, the single point of attachment 110 extends around the circumference of the outer surface 75 of the introducer member 12; however, FIGS. 18-18A depict an embodiment having more than one point of attachment 110 between the sleeve 13 and introducer member 12. The introducer member 12 can also be integrally attached to the sleeve 13, thus forming an arrangement of unitary construction.

As shown in FIGS. 1-4, the introducer assembly 11 is intended for use with a separate second member 15, hereafter referred to as the inner member, that is introduced through the passageway 20 of the introducer member 12 and into a bodily passage 26 (FIG. 4), such as the common bile duct or other passage. This inner member 15 can include any of a number of medical devices such as catheters, introducer sheaths, cannulae, stents, endoscopes, retrieval or surgical devices, etc. A portion of the sleeve body 76, referred to herein as the second portion 107, resides within the passageway 22 of the inner member 15 as the inner member is introduced into the bodily passage 26. The first portion 106 of the sleeve 13 is generally defined as that part of the sleeve body 76 that typically remains outside of the inner member passageway 22 after the sleeve 13 has been loaded. The second portion 107 is typically inverted or preloaded into the passageway 22 with that portion of the sleeve being eversible from the passageway 22 as the inner member 15 is advanced relative to the introducer member 12, to which the first end 25 of the sleeve 13 is attached. As used herein, the terms 'evert' or 'eversible' refers to the process by which the sleeve 13 unfurls, unfolds, invaginates, or otherwise exits the passageway 22 into which it resides, upon which time the sleeve 13 turns back on itself and conforms over the outer surface of the inner member 15, forming a barrier between the inner member 15 and the inner surfaces 28 of the bodily passage 36.

The overall length of the second portion 107 is largely determined by how far the inner member 15 is typically advanced into the bodily passage 26 during a particular procedure. The second end 64 of the sleeve is either completely unattached to the inner member 15 as it resides in the passageway 20, or is releasably secured in a manner such that the second end 64 is completely eversible from the passageway 22 of the inner member if necessary or so desired. Movement of the inner member 15 relative to the introducer member 12 is therefore, not normally limited by the length of the sleeve 13 and the introducer member 12, and the sleeve 13 can be removed from the patient or treatment site separately from the inner member 15 once the sleeve 13 has completely everted from the passageway 22. The introducer member 12 can comprise an elongate catheter, as shown in the illustrative embodiment, that houses the inner member 15, or it can be much shorter in length, as shown in later examples.

The length and shape of the sleeve can be quite variable, depending on the application. In the illustrative embodiment of FIGS. 1-4, which is used as a biliary catheter for an ERCP procedure in an adult patient, the sleeve is tubular and typically measures from 6-10 cm in length, preferably 7-8 cm, so that the inner member can cannulate both the opening of the duct and any strictures that may exist therein. Preferably, it should not be so long that it cannot completely evert from the inner member 15 during the procedure, since in this particular embodiment, removal of the sleeve is desired after the inner member is in position. Other procedures may require a longer sleeve 13. For example, the sleeve 13 used to introduce a standard feeding tube, e.g., a nasal-gastric (NG) or nasal-jejunal feeding tube, would be more in the 20-40 cm range, more preferably around 30 cm. The sleeve 13 is used to protect the feeding tube through the nasal passage past the deviation of the septum until it reaches the back of the throat where natural peristalsis takes over and helps to urge the feeding tube downward through the esophagus and into the stomach or jejunum. To assist natural peristalsis, the sleeve 13 or other portion of the introducer apparatus 10 can be provided with a surface structure having a bidirectional coefficient of friction such as disclosed in a pair of co-pending applications, both entitled, "Medical Instrument Having Bidirectional Coefficients of Surface Friction," U.S. Ser. No. 08/989,413, filed Dec. 12, 1997 and U.S. Ser. No. 09/184,331 filed Nov. 2, 1998.

A shorter sleeve, e.g., 7-10 cm may be desired for nasal introduction if the inner member is merely serving as a short conduit for the subsequent introduction of another device, such as an endoscope, therethrough. The second device can then be introduced much more comfortably than would be otherwise possible. Conversely, a much longer sleeve, e.g., 150-160 cm, might be used for a colonic procedure. Ideally, the sleeve for a particular application, should be properly sized such that it completely everts from the inner member, if so desired, to allow it to be removed while maintaining the inner member within the patient.

Continuing with the first embodiment, FIG. 2 depicts an introducer member 12 that is an elongated catheter in which the sleeve 13 has been completely inverted into the passageway 22 of the inner member 15 which in turn, coaxially resides within the passageway 20 of the introducer member 12. As shown in FIG. 3, the inner member 15 advances relative to the introducer member 12 with the distal end 36 or leading edge of the inner member 15 urging the sleeve 13 forward and thereby, pulling it out of the passageway 22 into which it has been loaded.

FIG. 4 show the introducer apparatus 10 being used within a patient. The introducer member 12 is positioned at the opening 27 of a bodily passage 26 into which the inner member 15 is to be introduced. Holding the proximal portion 77 (FIG. 1) of the inner member 15 in place, the introducer member 12 is then urged in a proximal direction. Typically, this action causes the sleeve 13, which sheaths the distal end 36 of the inner member, to grip the surface of the passage opening 27, thereby 'self-advancing' the inner member 15 as the introducer member 12 is 'retracted' (as shown). In these instances, the introducer member 12 does not actually move any significant distance from the opening, despite the rearward force be applied, but rather, the inner member 15 is advanced forward into the bodily passage 26 although it is not actually being directly advanced by the operation. Thus, the inner member 15 is described as 'self-advancing.' In selected embodiments or certain instances, the operator may need to directly advance the inner member 15 in order to have the sleeve 13 evert and lay down a protective track; however, the sleeve still provides the same protective function. For each of the illustrative embodiments, the sleeve 13 lays down a track, much like the way a military tank or bulldozer moves, such that the advancing inner member 15 frictionally slides against the protective sleeve 13 itself instead of directly contacting the lining 28 of the bodily passage 26. Because the sleeve 13 does not slide against the internal lining 28 of the bodily passage 26, there is minimal irritation and trauma to the opening 27 and bodily passage 26 during its initial introduction. The sleeve 13 protects the bodily passage 26 for a distance up to its own length, after which, it completely everts from the inner member 15 and any further advancement will typically result in normal frictional contact between the inner member 15 and the bodily passage 26. In the case of the biliary tree, it may only be important to provide protection for a short distance to traverse the Papilla of Vater, or it may be necessary or desirable to extend this protection further into the duct such as to cannulate a stricture. For certain applications, the sleeve 13 should completely or functionally evert from the passageway 22 of the inner member 15, or a particular application may not require that it does so.

With respect to the embodiment of FIG. 1, which is configured for accessing the biliary tree, the introducer member 12 should be at least 150 cm for an adult patient, typically 157-160 cm. The introducer member 12 normally must be removed from the patient while the inner member 15 remains in place. To accomplish this, the inner member 15 is made at least twice as long as the introducer member 12 such that the entire length of the introducer member 12 can remain over the inner member 15 and extend outside the patient. This is especially useful when there is a proximal connector 21 on the inner member 15 of this embodiment which may not permit removal of the introducer member 12 thereover. The proximal connector 21, such as a luer fitting, is useful in this embodiment because the injection of contrast media, which would be infused through the inner member 15, is typically important in ERCP procedures. A removable connector may be used, such as a Tuohy-Borst adaptor, that can be unscrewed and removed to allow removal of the introducer assembly 11, then reattached. A reattachable proximal connector 21 is particularly advantageous when the inner member 15 is made long (e.g., 400 cm) to allow the introducer member over the inner member, which remains in place within the patient. Once the introducer member 12 is discarded, the long inner member 15 can be cut to a more manageable length (e.g., closer to 200 cm) before replacing the proximal connector 21.

Figure 5:
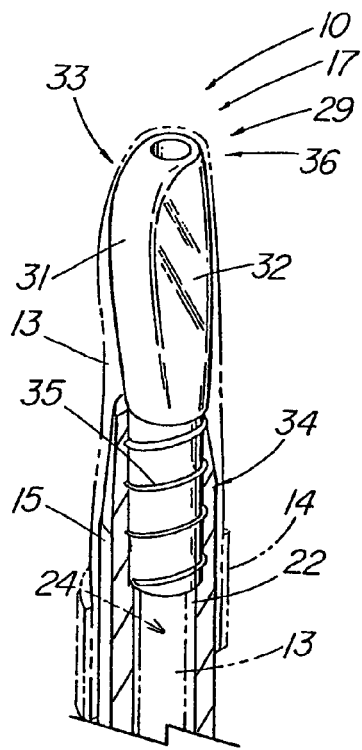
FIG. 5 depicts an enlarged partially sectioned view of an embodiment of the present invention having an asymmetrical tip.

In certain clinical procedures, it is advantageous to be able to direct or deflect the tip of the inner member as it is being advanced into the bodily passage, for example, to negotiate a particular branch when confronted with a bifurcation. FIGS. 5-10 depict various means of causing the inner member 15 to deflect in one particular direction over the other. In the embodiment of FIG. 5, a separate distal tip 29 is affixed at the distal end 36 of the inner member 15. As depicted, the distal tip 29 is configured to be an asymmetrical-shaped tip 30 which includes a proximal portion 34 that is inserted into the passageway 22 of the inner member and a distal portion 33 that forms the leading edge of the inner member 15. The distal portion 33 of the asymmetrical-shaped tip 30 is divided longitudinally into a first side 31 and a second side 32. In the illustrative example, the first side 31 is considerably more rounded than the flattened second side 32. As a result, the enlarged first side 31 provides more drag against the sleeve 13 than the second side 32 as the sleeve 13 is everting out of the inner member 15, which in turn, causes the distal end 36 of the inner member 15 to laterally deflect toward the direction corresponding to the first side 31.

Figure 6:
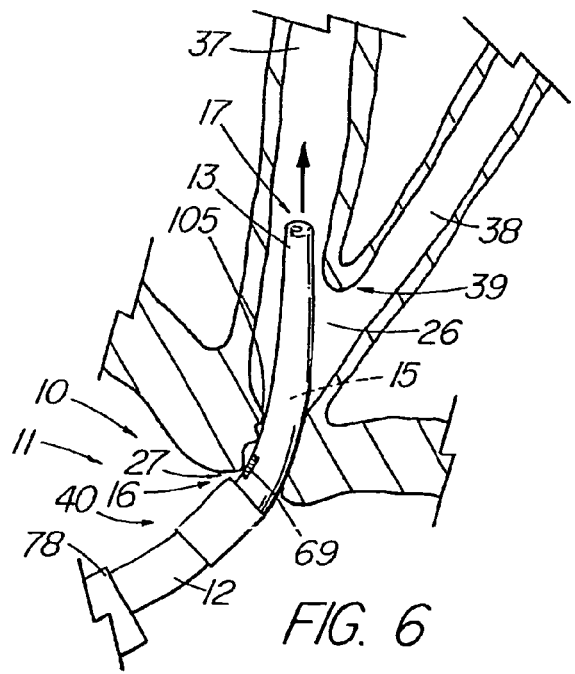
FIG. 6 depicts the embodiment of FIG. 5 being directionally guided within the body of a patient.

FIG. 6 depicts a laterally deflectable embodiment of the present invention accessing the bile duct. When the introducer 11 is advanced from an endoscope 78 and placed at the Papilla of Vater 27, the opening to the common bile duct 26, there is a marker 69 that indicates the direction in which the inner member 15 will deflect. To accomplish this, it is essential that the inner member 15 and introducer member 12 be aligned such that the means for deflection, whether part of the inner member 15 or the sleeve 13, is aligned with the marker 69 printed on the sleeve 13 or introducer member 12. This can be done by providing guide marks (not shown) on the proximal area of both the outer and inner members 12, 15 such that they can be rotated into alignment prior to advancement of the inner member 15. Once alignment has occurred and the position of the marker 69 is established endoscopically, the inner member 15 is advanced into the common bile duct 26 where it deflects into the bile duct 37 as desired, avoiding the pancreatic duct 38. To access the pancreatic duct 38 instead, the introducer assembly 10 would be simply rotated such that the marker 69 is positioned approximately 180° in the opposite direction. Alternate methods of providing a visual marker on the sleeve 13 would be to place a radiopaque marker on either the sleeve 13, the inner member 15 or the introducer member 12 such that the orientation of the asymmetrical tip 30 can be determined under fluoroscopy when contrast media is injected into the biliary tree. It should be noted that the natural folds of tissue 105 just inside the common bile duct 26 may be utilized to help provide increased grip on the sleeve 13, thereby pulling the inner member 15 preferentially toward the bile duct 37 branch.

Figure 7:
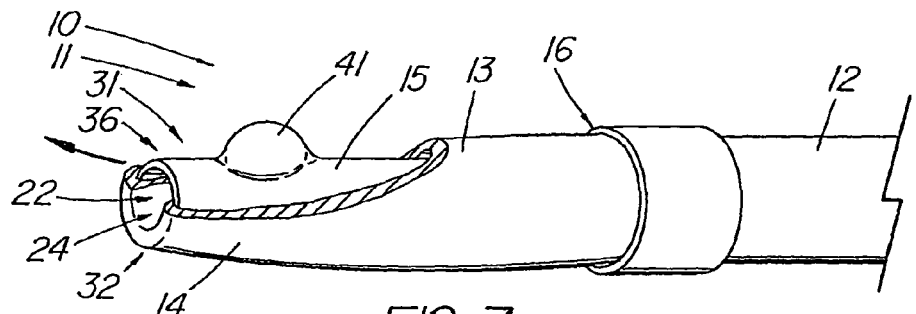
FIGS. 7-8 depict partially sectioned side views of various embodiments of the present invention having asymmetrical tips.
Figure 8:
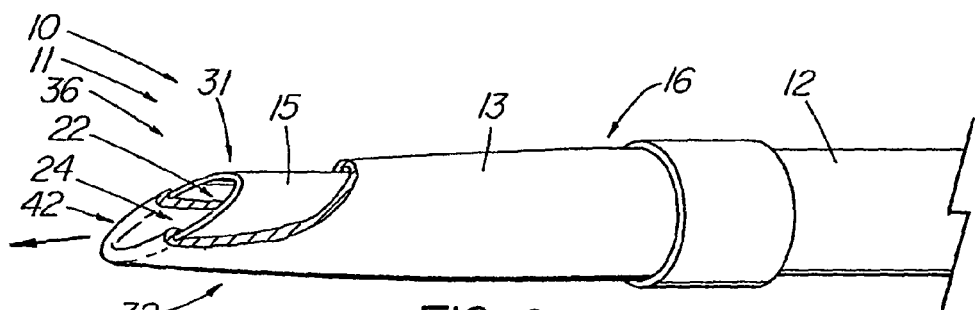

Besides incorporating a separate asymmetrical tip 30 to cause the advancing inner member 15 to deflect, as shown in FIG. 5, the distal end 36, or the region thereabout, of the inner member 15 itself can be configured (FIGS. 7-8) to provide unequal drag between the different sides 31,32 of the inner member, thereby causing the sleeve 13 to pull the inner member 15 laterally in a particular direction as it advances. In the embodiment of FIG. 7, the first side 31 of the inner member 15 includes a lateral protuberance 41 that increases resistance to the sleeve 13 passing thereover. The resistance differential relative to the second side 32, which lacks a protuberance 41, causes the inner member to deflect toward the first side 31. In the embodiment of FIG. 8, the distal end 36 of the inner member 15 includes a bevel 42 to provide different degrees of resistance to the sleeve 13 between the first side 31 and the second side 32 of the inner member. The long second side 32 of the bevel 42 provides increased resistance over the first side 31, therefore causing the sleeve 13 to deflect the inner member 15 in that particular direction.

Figure 9:
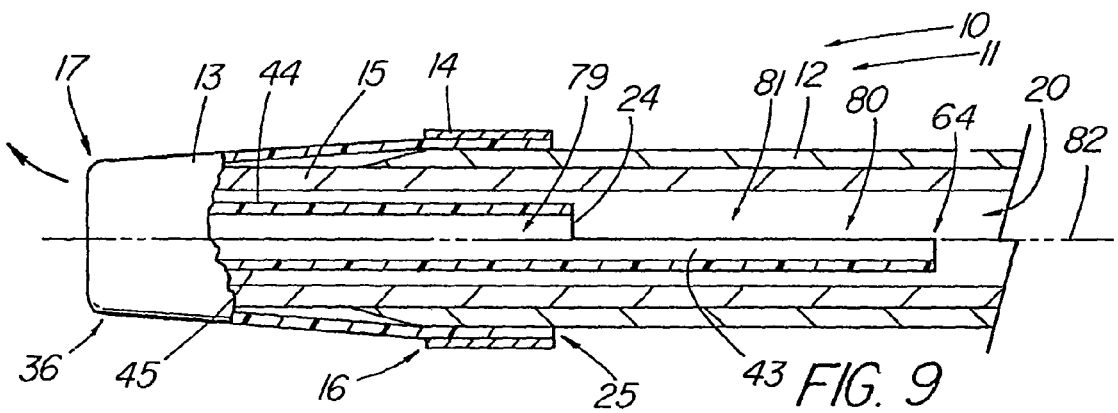
FIG. 9 depicts a partially sectioned side view of an embodiment of the present invention with an asymmetrical eversible sleeve.
Figure 10:
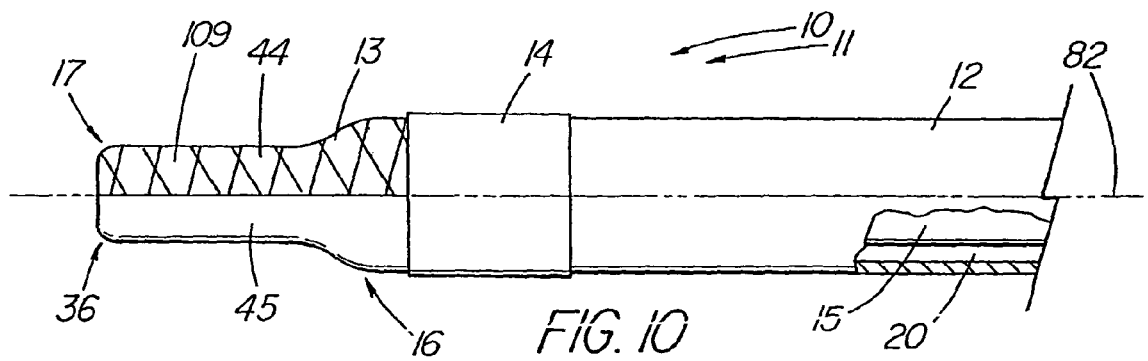
FIG. 10 depicts a side view of an embodiment having a sleeve with asymmetrical properties.

In addition to modifying the inner member 15 to achieve controlled directionality during its advancement, the sleeve itself 13 can be modified to achieve similar results. In FIG. 9, a sleeve is shown having a distal portion 79 that is tubular in shape and a proximal portion 80 in which the material on one half is removed to create a partial sleeve 43 which is semi-circular in cross-section during deployment of the apparatus 10. In this design, the full sleeve 13 or distal portion 79 is used to cannulate the opening to the bodily passage, whereby as the partial sleeve 43 portion everts, a situation is created in which there is a friction differential between the two sides 31, 32 of the inner member 15 that results in the inner member 15 being laterally deflected in the direction of the open portion 81 of the sleeve 13. Another means of accomplishing this effect is depicted in FIG. 10 whereby the sleeve is divided longitudinally into two halves 44, 45, each having different properties. In the illustrative embodiment, the first half 44 of the sleeve comprises a porous material with a plurality of apertures 109, such as a fabric mesh, while the second half 45 comprising a material more suitable for friction reduction. One purpose of the porous material would be allow contrast media to be pushed through the apertures 109 into the bodily passage to improve imaging of the target site for diagnosis or treatment. A large open mesh, e.g., 0.02-1.0 mm, would also allow drugs to be infused into the bodily passage. The amount of porous material can range from a narrow longitudinal strip, to an area comprising the majority of the circumference of the sleeve 13. Another clinical application for a large open mesh would be for obtaining cytology samples, whereby withdrawal of the sleeve within the bodily passage traps cells within the apertures 109 in the mesh and allows the cells to be collected for laboratory analysis.

In another variation of the embodiment of FIG. 10, the two halves 44, 45 of the sleeve 13 can given a different coefficient of friction, which causes the sleeve to deflect toward either the first side 31 or the second side 32, depending on which half of the sleeve 44, 45 offers the most resistance against the inner member 15 as the sleeve 13 as it is being everted. The first and second sleeve halves 44, 45 can either be made of different materials that are joined along the longitudinal axis by an appropriate means such as stitching, welding, gluing, etc., to form a tubular composite sleeve 13, or a sleeve 13 of a single material can be treated to increase the coefficient of friction on one side. For example, the material could be mechanically or chemically roughed to increase friction; a second material, such as silicone beads, could be applied to the surface to increase friction; or a lubricious material could be added to reduce friction on a particular side.

Figure 23:
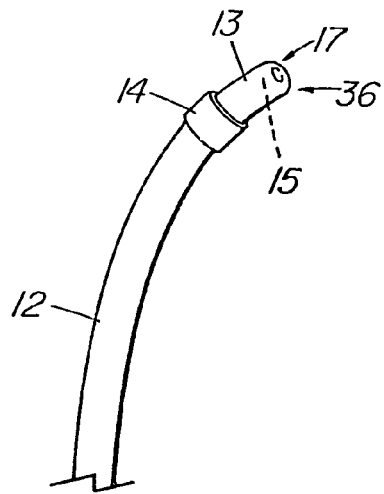
FIG. 23 depicts a side view of an embodiment of the present invention having a preformed introducer member.
Figure 24:
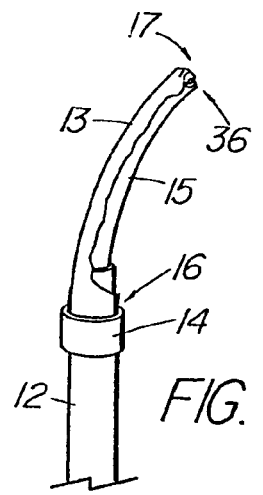
FIG. 24 depicts a side view of an embodiment of the present invention having a preformed inner member.

Another means of adding directionality to the introducer apparatus 10 is to incorporate a desired amount of curvature to a component thereof during its manufacture. FIG. 23 depicts an introducer apparatus 10 in which the introducer member 12 has been preformed with a particular curvature to improve accessibility to a target site in certain clinical situations. It might be desirable to limit the curvature to the very distal portion or the curvature might extend over a greater portion of the inner member 15. The inner member 15 itself can be preformed with a curvature as well, as depicted in FIG. 24 to aid in certain procedures, especially an ERCP, where the ability to successfully navigate a bifurcation may be required. In the illustrative embodiment, the introducer member 12 has sufficient integrity relative to the inner member 15 (i.e., stiffer materials, increased wall thickness, etc.) that it acts to constrain the curved inner member 15 into a straight configuration, wherein the inner member assumes its predetermined shape upon advancement from within the introducer member 12. In another embodiment, the curved inner member 15 would force the otherwise straight introducer member 12 to assume the inner member's predetermined shape. In still another embodiment, both the inner member 15 and introducer member 12 can be both given a predetermined curvature, which may approximately match that of the other. One result of added curvature to both the outer and inner member 12, 15 would be to allow for an overall double curvature wherein the introducer member 12 permits a lateral access in one direction, while the advancing inner member 15 can positioned such that it deflects back in a second direction (e.g., an S-curve). It should be noted that in some applications, such as an ERCP procedure, the inner member 15 must be made sufficiently flexible to bend back on itself when it cannot find a suitable passageway, thereby not creating a false passage. Other methods for curving the inner member 15 include having the sleeve 13 extruded such that it includes curvature of its own. If the sleeve 13 has sufficient linear strength or stiffness and the inner member 15 is sufficiently pliable, the curved sleeve 13 would force the inner member 15 to deflect in the direction of the curvature of the sleeve 13, much like the example depicted in FIG. 24 which is also provided to illustrate a pre-curved inner member.

Figure 34:
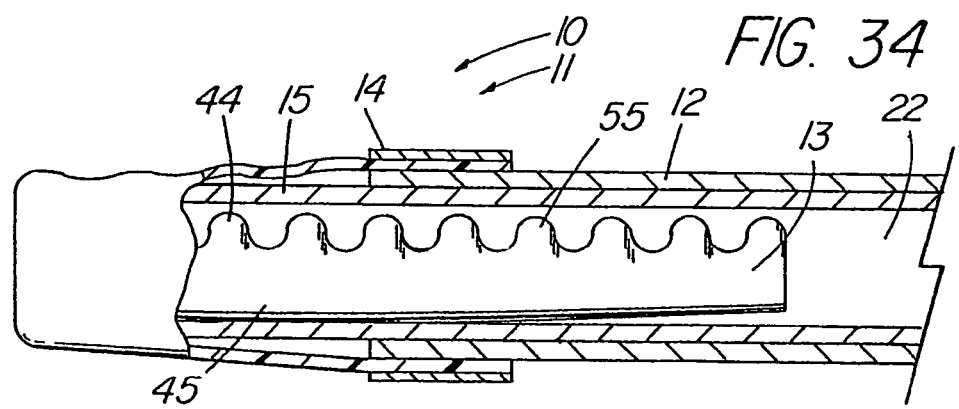
FIG. 34 depicts an embodiment of the present invention in which the sleeve is partially pleated.

FIG. 34 depicts another sleeve configuration for preferentially directing the inner member 15, whereby the sleeve 13 is extruded or shaped such that one half 44 includes pleat or folds 55, while the other half 45 is of the typical smooth, cylindrical shape. Under selected conditions, the inner member 15 would generally tend to deflect in the direction oriented with the second, smooth half 45 of the sleeve.

Figure 11:
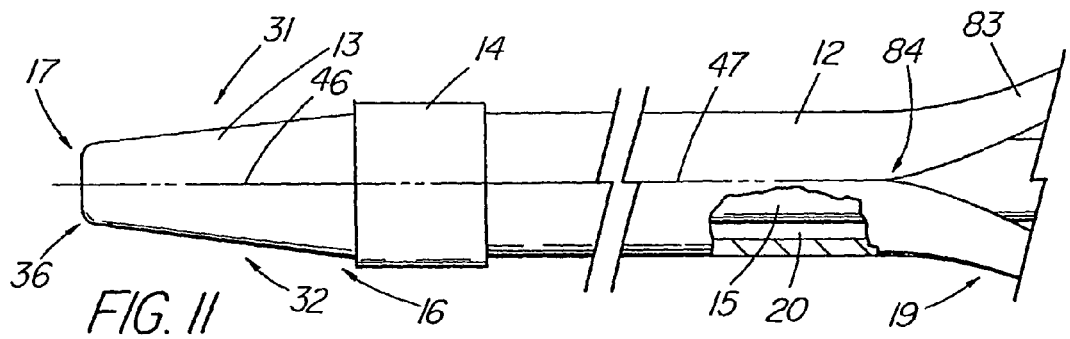
FIG. 11 depicts a side view of an embodiment with a splittable introducer apparatus and sleeve.
Figure 27:
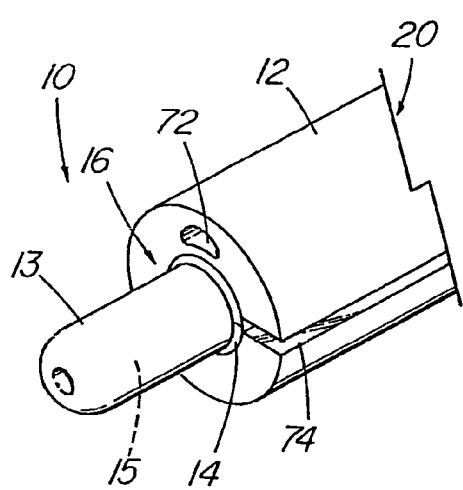
FIGS. 26-27 depict distal end pictorial views of embodiments of the present invention having a multiple lumen introducer member.

As discussed, using the present invention in certain types of procedures may require that the introducer member 12 and sleeve 13 be removed from the patient, or at least from around the inner member 15, while the inner member 15 remains in place. In addition to making the inner member 15 such that the introducer member 12 can either be removed over the proximal end 19 (i.e., a detachable hub) or the inner member is at least twice as long as the introducer member 12, another methods would include making the introducer member 12 and sleeve 13 splittable as depicted in FIG. 11 such that they can be peeled back from the proximal end 19 and removed without requiring disruption to the inner member 15. One preferred material for a splittable introducer member 12 is molecularly oriented (non-isotropic) polytetrafluoroethylene (PTFE), such as that used in the PEEL-AWAY™ Introducer Sheath (Cook Incorporated, Bloomington, Ind.). The advantages of the material is that it does not require a prescored line and as it is being split open as the progressive tear maintains a straight and predictable pathway. At the proximal end 19 of the introducer member 12, the sheath has been modified to comprise two opposing ears 83 or tabs that are divided by opposing cut points 84. The operator grabs the ears 83 and pulls them apart from each other, starting the split at the cut points 84. Once the splitting action has commenced along opposing predetermined split lines 47, it progresses distally as the two halves of the introducer member 12 sheath are pulled apart. Depending on the design, the split continues through the sleeve attachment 14 and splits the sleeve 13, which may include a tear line 46 such as a perforation, or the split may stop at the attachment point or sleeve and the operator will then manually split the remainder of the introducer assembly 11 that is now outside the patient, such as with a scalpel, taking care not to nick the inner member 15. A third method of removing the introducer member 12 from over the indwelling inner member 15 is depicted in FIG. 27. The introducer member 12 includes a longitudinal opening 74 or split extending the length of the introducer member 12 through which the inner member 15 can be removed from the passageway 20 thereof. The introducer member 12 can then be removed from the patient while the inner member 15 remains in place.

Figure 12:
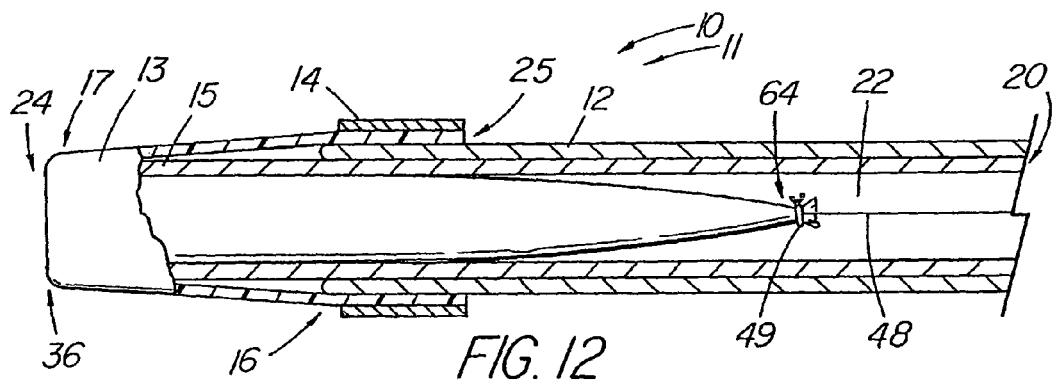
FIG. 12 depicts a partially sectioned side view of an embodiment of the present invention having a tethered sleeve.
Figure 13:
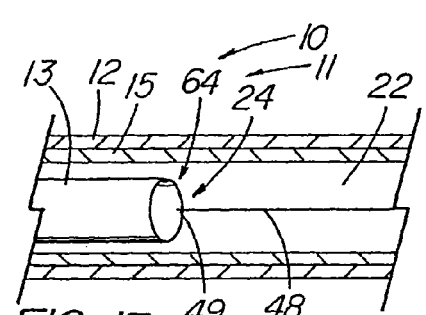
FIG. 13 depicts a partially sectioned detail side view of an embodiment of the present invention with an open tethered sleeve.
Figure 14:
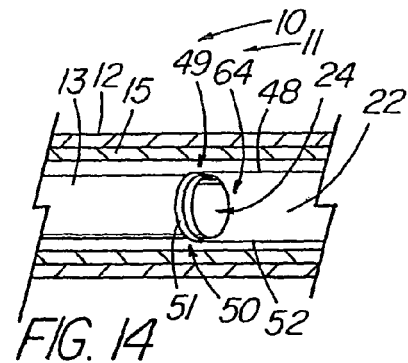
FIG. 14 depicts an enlarged side view of a second embodiment of the present invention having an open tethered sleeve.

FIG. 12 depicts an embodiment of the present invention in which the sleeve 13 is reloadable by use of a tether 48 attached to the second end 64 of the sleeve 13 and where the attachment point 49 includes a knot or other means to secure the tether 48 to the sleeve 13. The sleeve 13 remains basically eversible from the passageway 22 of the inner member 15; however, the inner member 15 is limited in it's forward movement once it does. The everted sleeve 13 can advantageously retrieved by grasping the accessible portion of the tether 48 and pulling in a proximal direction. This pulls the sleeve 13 back into the passageway 22 whereby the sleeve 13 again becomes inverted into the inner member 15, making available to be used again, if necessary or so desired. To maintain patency of the sleeve 13, the embodiment of FIG. 13 includes a tether 48 where the attachment point 49 to the sleeve 13 is located along only one side of the second end 64 such that the sleeve passageway 24 remains in an open condition and thus, better able to receive a wire guide, deliver contrast media, etc. A second tether 52 and attachment point 50 can be added to add stability and maintain patency as depicted in FIG. 14. An annular ring 51 can further serve to hold the sleeve passageway 24 open and provides an anchoring point for the attachment points 49, 50 of the respective tethers 48, 52. If the annular ring 51, is made of an elastic materials, it is possible for the inner member 15 to push through the annular ring 51 and not be limited advancement of the inner member 15, especially if the annular ring 51 is given a larger diameter than the inner member 15 and compressed within the passageway 22. If not, the ring 51 will typically stop at the distal end 36 of the inner member 15, limiting the further advancement thereof.

Figure 15:
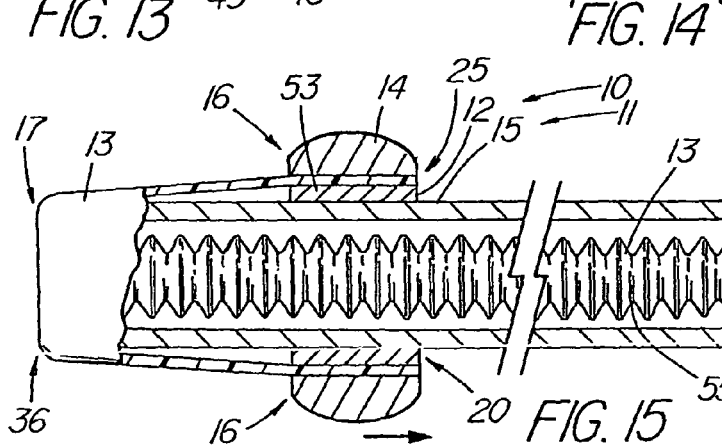
FIG. 15 depicts a partially sectioned side view of an embodiment of the present invention having a pleated sleeve.

FIG. 15 depicts an embodiment of the present invention in which the sleeve 13 is configured to include a series of pleats 55, resulting in the body 76 of the sleeve 13 become somewhat accordion-shaped while inverted into the passageway 22 prior to deployment. The pleats 55 permit the sleeve to unfold and expand longitudinally as it everts. This can be especially useful when the eversible sleeve must extend over a considerable distance, such as for a small bowel nasal feeding tube which can be 150 cm in length. The primary value of folding the sleeve to reduce its length is to provide less drag between the sleeve 13 and the inside of the inner member passageway 22, since a long sleeve 13 is more difficult to pull out of or load into the inner member 15 due to the increased frictional load.

Figure 16:
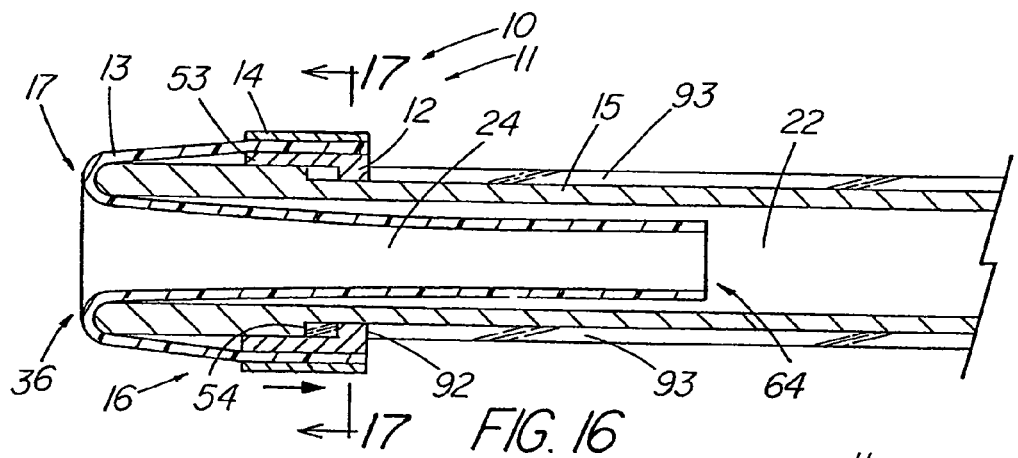
FIG. 16 depicts a cross-sectional view of an embodiment of the present invention having a ring-like introducer member.
Figure 17:
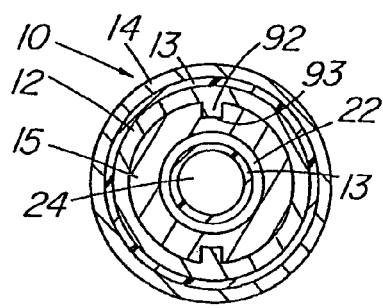
FIG. 17 depicts a cross-sectional view of an embodiment of FIG. 16, taken along line 17-17.

FIGS. 15-17 show a modification of the apparatus 10 in which the introducer member 12, rather than comprising a elongated tube, is an external ring 53 or carriage-like structure that is slidable with respect to the inner member 15 that is to be introduced into the bodily passage. As shown in FIG. 16, the external ring 53 can optionally be prevented from being removed from the distal end 36 of the inner member by inclusion of a stop 54 that is incorporated into the inner member 15. Additionally, the external ring 53 can include at least one projection 92 that fits within a groove 93 on the inner member 15 such that the external ring 53 cannot twist or rotate relative to the inner member 15 which could also result in the twisting of the sleeve 13. In its simplest form, the external ring 53 can be made integral with the sleeve 13 material such as by forming a thickened portion thereof at or near the first end 25 of the sleeve 13. Having the introducer member 12 comprise a relatively short external ring 53 rather than an elongated tubular member is preferable, or at least possible, in applications where the entire introducer member 12 is outside the patient's body, or nearly so, such as a nasal tube or urinary catheter introduction, or when accessing the lower gastrointestinal tract via the rectum. In these instances, the clinician can grasp the external ring 53 which generally abuts the introduction site, whereby the inner member 15 spontaneously advances or is manually advanced into the bodily passage. In a remote access situation as with the biliary system, the introducer member 12 must be sufficiently long such that the proximal end 19 is outside the body (FIG. 1) so that it can be manipulated from that point, rather than from within the duodenum.

In a related embodiment shown in FIG. 37, the inner member 15 comprises a container 115, such as a bottle, used to supply fluid used in the administration of an liquid agent, such as to perform an enema. The bottle 115 includes a proximal reservoir portion 116 which narrows distally to form a neck portion 117 that is inserted into the patient. The introducer assembly 11 includes the sleeve 13, the sleeve attachment 14, and outer member 12, which in the illustrative embodiment, comprises a ring-like member 53 with a proximal collar. The ring-like member 53 is sized larger than the anal orifice 118 and is designed to abut the peri-anal area 119. The illustrative embodiment is configured for self-delivery whereby the patient gently inserts the distal tip 36 of the bottle (covered by forward edge of the sleeve 17) into the anal orifice 118. The sleeve 13, provided to reduce friction and discomfort caused by the insertion of the bottle 115, then spontaneously everts as the neck 117 of the bottle is drawn through the anal sphincter 121 into the rectum where the contents of the bottle 115 are delivered. The wider reservoir portion 116 can provide a stop to ensure that the neck portion 117 traverses the anal sphincter 121 without extending too far into the rectum 120. The sleeve 13 can either be unattached within the interior passageway 22 of the bottle 115 or be eversible by attaching to the inner member 15 in a manner such that it does not obstruct fluid flow therethrough (i.e., glued or otherwise bonded against the passageway 22 wall or about the distal end 36. It is not necessary to attach the ring member 53 to the bottle 115, which can be packaged together with plastic wrap or some other means to both keep the apparatus sterile and maintain the ring member 53 in a fixed pre-delivery position. At deployment, the neck 117 of the bottle advances through the ring member 53, which is held stationary against or adjacent to the peri-anal area 119. The same concept, i.e., container 115 with eversible sleeve 13, can be applied for delivery of therapeutic agents via the nasal passages or elsewhere in the body and maybe include a syringe, bag, pump, or other container adapted to hold and deliver a liquid, gas, or a suitably formulated solid material. The neck portion 117 may comprise various shapes and materials depending on the desired application.

FIGS. 18-18A depict an embodiment wherein the introducer member 12, rather than being a coaxial outer tube or ring, comprising a pair of longitudinal attachment strips 56, such as flat wires or strips of material, that reside in opposing grooves 57 or channels formed into the outer surface of the inner member 15, and through which the inner member 15 passes as it advances into a bodily passage. The attachment strips 56 are secured to two oppositely oriented attachment points along the sleeve 13 with an attachment mechanism 14 such as adhesive, stitching, etc., or they are tightly biased against the sleeve 13 such that when the attachment wires 56 are retracted by the operator, the inner member 15 advances through the bodily passage until the sleeve 13 fully everts. The attachment wires 56 may then be fully retracted along and within the grooves 57 to completely remove the sleeve 13 from the patient. Optionally, the attachment strips 56 can be conjoined at or near their proximal ends or to allow them to be retracted at the same rate. In should be noted that the number of longitudinal attachment strips 56 is not critical to the invention. Furthermore, the embodiments of FIGS. 18-18A show that the sleever fixation mechanism 12 or introducer member need not be a tubular or an annular structure, but rather, can include any structure or series of structures, including an array of barbs or other fixation devices, that can attach about the first end 25 of the sleeve and maintain the first portion 106 of the sleeve outside the opening of the bodily passage, while facilitating the introduction of the inner member 15 therethrough. For example, barbs or other structures of similar function can be configured to engage tissue about the opening of the bodily passage to facilitate introduction of the inner member, then disengage when the sleeve 13 is to be discarded. In this sense, the array of barbs collectively form the sleeve fixation mechanism 12, which can also be defined as the introducer member, with the inner member 15 being advanced therethrough.

Figure 19:
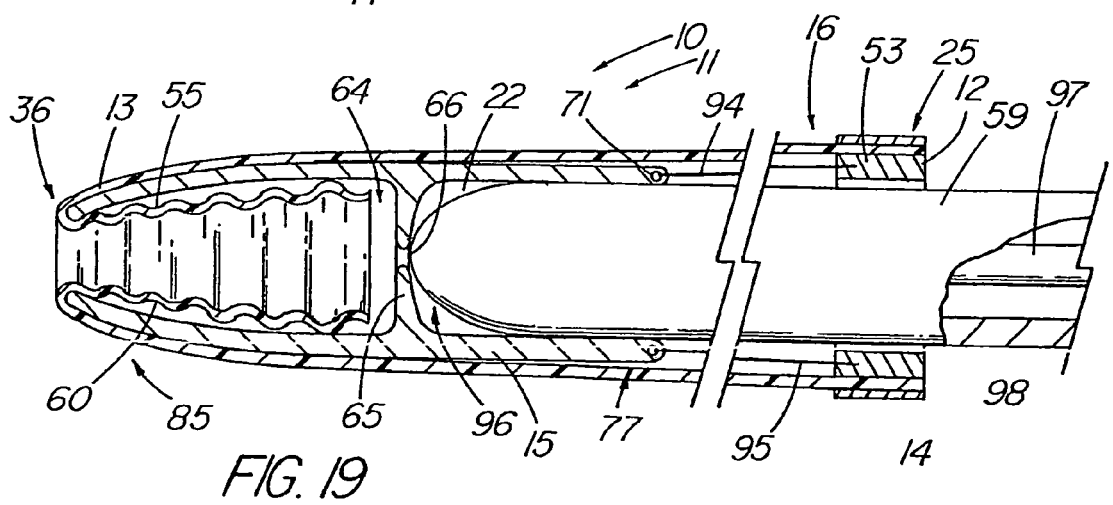
FIG. 19 depicts a partially sectioned view of an embodiment of the present invention for introducing a third member.

FIG. 19 depicts an introducer apparatus that can be used with a third member or device 59, such as nasal-gastric (NG) or nasal-jejunal (NJ) feeding tube, endoscope etc. of various sizes. Such devices can be introduced while having the benefit of the protective sleeve, yet without the sleeve directly cooperating with the third device 59. In the illustrative embodiment, the introducer member comprises an external ring 53 and the sleeve 13 inverts into an inner member 15 that is separate from the third device 59. The inner member 15 acts as a distal cap that fits over the distal end 96 of the third device 59 being introduced. The inner member 15 can be advantageously made of a resilient material, such as silicone, such that it can stretch over the third device 59 that is inserted thereinto, although less-resilient materials can be used if tight cooperation between the second and third members 15, 59 is not necessary. The inner member 15 comprises a distal sleeve chamber 60 that houses the loaded sleeve 13, and a receiving chamber 70 into which the third device 59 is inserted. The medical device 59 is advanced through the introducer member 12 (external ring 53) and into the receiving chamber 70 until it abuts the chamber septum 65 which divides the two chambers 60, 70. The external ring 53 has a complete circumferential attachment 14 to the sleeve 13 which is inverted into the distal sleeve chamber 60. The external ring 53 is also attached to the proximal portion 77 of the inner member 15 via a first and second deployment tether 94, 95 at attachment sites 71 on the introducer member 12, usually 180° apart.

One example of how the embodiment of FIG. 19 is placed is that of a NG feeding tube 59. The distal ends 16, 36 of the outer and inner members 12, 15 are placed into the opening of the nasal passage and the external ring 53/introducer member 12 is typically urged in a proximal direction to cause the inner member 15 and NG feeding tube 59 into be introduced into the nasal passage. The sleeve 13 protects the lining of the nasal passage from trauma resulting from the advancing inner member 15 and NG feeding tube 59 as they advance toward the stomach. Deployment of the NG feeding tube 59 from the inner member occurs within the esophagus, once the distal end 36 of the inner member 15 has passed through the sensitive nasal passages. At this point, the tethered ring 53 is pulled backward until the NG tube 59 pushes through the aperture 66 in the chamber septum 65, then into the distal sleeve chamber 60, and out the distal end 36 of the inner member 15. The external ring 53 and tethered sleeve 13 are pulled over the external surface of the indwelling NG feeding tube 59 where they are cut free, once outside the patient. To help ensure that the NG tube has sufficient column strength to penetrate chamber septum 65, a stiffening stylet 97 can be introduced into the passageway 98 of the NG tube to improve its pushability, whereby it is removed once the NG tube 59 has been advanced through the distal end 36 of the inner member 15.

Figure 31:
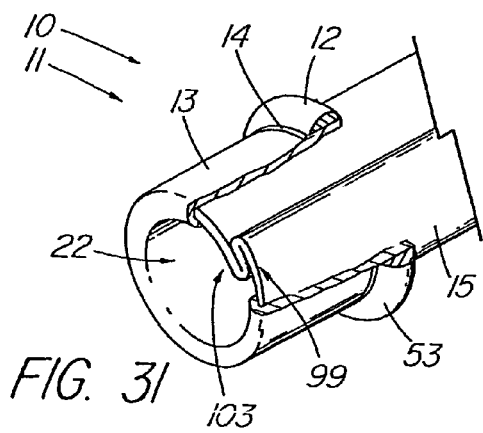
FIGS. 31-33 depict partially cutaway pictorial views of embodiments of the present invention having an expandable inner member.
Figure 32:
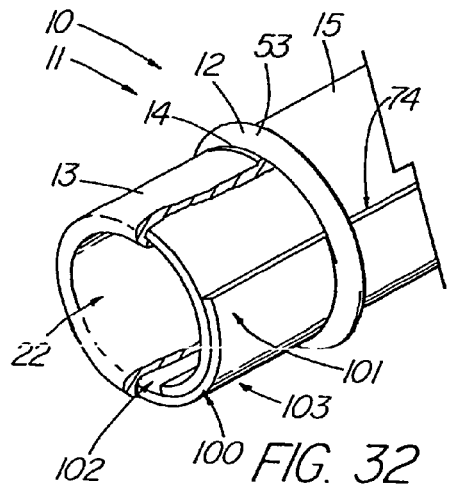
Figure 33:
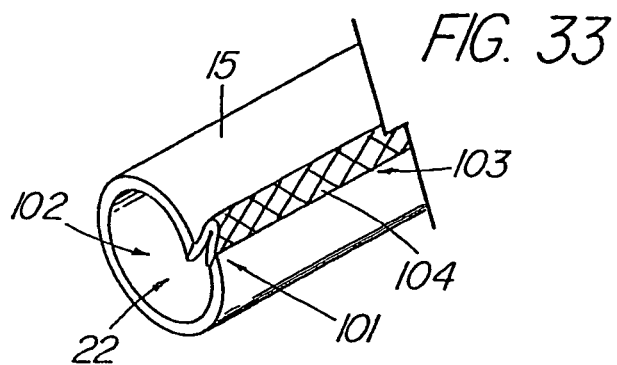

More simplified embodiments of the universal introducer concept can be found in FIGS. 31-33. As depicted, the inner member 15 includes an longitudinal expansion zone 103 that allows the inner member 15 to radially expand, especially following removal of the introducer assembly 11, to allow variously-sized devices of a larger diameter to be introduced therethrough. The embodiment of FIG. 31 includes an inner member 15 with longitudinal expansion zone 103 comprising an expansion pleat 99. The expansion pleat 99 represents an invagination in the wall of an inner member 15 which is then folded over to create an inner member 15 of a first, unexpanded diameter as shown in the figure. The introducer member 12 (external ring 53) acts as a containing mechanism to maintain the inner member 15 in the first diameter. When the introducer member 12 and sleeve 13 are removed from over the inner member 15, it permits a third member or device 59 (like that shown in FIG. 19) to be introduced through the inner member, which then assumes a larger, second diameter. The expansion pleat 99 unfolds to allow passage of a device (e.g., an NG tube) that has a larger diameter than the first diameter of the inner member 15, these advantageously providing the combination of a smaller introducer with a larger, optimally sized indwelling device.

FIG. 32 depicts another embodiment of an expandable inner member 15 having a longitudinal opening 74 or split in which the longitudinal expansion zone 103 comprises an overlapping area 100 of the first edge 101 and the second edge 102 defined by the longitudinal opening 74. In the illustrative embodiment, the first edge 101 is folded over the second edge 102 to create the overlapping area and give the inner member a first, unexpanded diameter that is maintained by the external ring 53 of the introducer member 12. When the introducer member 12 and sleeve are removed, the second, inner edge 102 and first, outer edge are able to slide toward one another, thereby allowing radial expansion of the inner member 15 to the second, expanded diameter for passage of a larger diameter device. In a variation of this embodiment, depicted in FIG. 33, the first and second edge 101,102 of the cut tube can be attached via an expandable bridge 104 of a second and usually more flexible material. The expandable bridge 104 of the longitudinal expansion zone 103 can extend underneath the first edge 101, forming an overlap 100 similar to FIG. 32, or the first and second edges 101, 102 may not actually overlap. In the latter instance, expansion can result from folding or invaginating the flexible material of the expandable bridge 104 to permit radial expansion of the inner member 15, or relying on elastic properties of the expandable bridge 104 to allow the inner member 15 to assume a second, expanded diameter when a larger diameter device is passed therethrough.

FIG. 36 depicts an embodiment of a nasal introducer used to cannulate the nasal passages 112 to introduce a third member or device 59, such as a nasal endoscope. Since the sleeve 13 does not need to be separately removed from the inner member 15, which is only introduced a relatively short distance to provide a conduit for passage of the third member 59, the second end 64 of the sleeve 13 is conveniently, but not essentially, affixed to the inner member 15. Because the second member 15 functions as introducer, it is generally preferable that the attachment 111 of sleeve 13 to the second member 15 be located and configured such that the passageway 22 of the inner member 15 remains substantially unobstructed to facilitate passage of the third member 59. FIG. 36 shows one example of such an attachment 111, which is affixed about the distal end 36 of the inner member 15 with the attachment 111 occurring within a groove 114 formed in the distal end 36 thereof, leaving the passageway 22 clear and unobstructed after the sleeve 13 has fully everted. It would still be within the scope and spirit of the invention for the attachment 111 to be located such that a portion of the sleeve remains within the passageway when the inner member 15 is fully extended, as long as the sleeve 13 is eversible to the point where the passageway 22 is not significantly or functionally narrowed or obstructed by the sleeve 13 and/or its attachment 111. The term 'eversible' should therefore be understood to be equivalent to the concept of being 'functionally eversible', whereby, unlike the Bidwell '670 device with its internal 'retention sled' to which the sleeve is attached, the sleeve and attachment of the present invention have the capacity to clear the passageway 22 to a sufficient degree as not to interfere with the passage of a third member 59 therethrough. Features described in the other accompanying embodiments may also have particular utility for the embodiment of FIG. 36, such as a channel 93 to prevent the introducer member 12 from rotating relative the inner member 15 (FIG. 16), and a preformed inner member 15 (FIG. 24) that facilitates navigation of the inner member 15 and/or third member 59 toward the nasopharynx 113.

Figure 35:
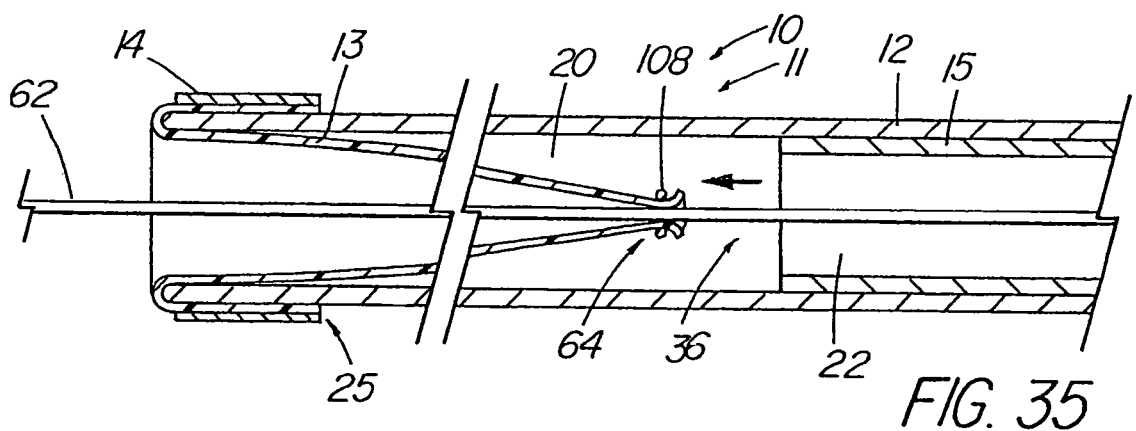
FIG. 35 depicts an embodiment of the present invention adapted such that it is not to be preloaded into an inner member.

FIG. 35 depicts an embodiment in which introducer member 12 and sleeve 13 can be introduced into the body without preloading the sleeve 13 into the inner member 15. In the illustrative example, the second end 64 of the sleeve 13 is attached to a wire guide 62 that was been preloaded into the introducer member 12. The sleeve 13 and wire guide 62 can be coupled such that the wire guide 62 can slide relative to the sleeve 13 or that the sleeve 13 is fixed over the wire guide 62. A sleeve attachment 108 is used, such as a small band, suture, adhesive, or other means of gathering and securing the second end 64 of the sleeve, which allows the sleeve 13 to become detached from the wire guide 62 when the advancing inner member 15 pulls it loose, either by sliding off the attachment member 108 from around the sleeve 13 (such as onto the wire guide) or causing an opening or detachment of the attachment member 108 to release the sleeve 13. By gathering and attaching the second end 64 of the sleeve 13 about the wire guide 62, the second end 64 is readily drawn into the passageway 22 of the inner member 15 as it tracks over the wire guide 62 upon advancing toward the distal end 16 of the outer member 12. While attachment of the second end 64 to the wire guide 62 facilitates capture of the sleeve 13 within the passageway 22 of the inner member 15, it is also possible to eliminate the wire guide 62, especially if not otherwise useful in the procedure, and gather the end 64 of the sleeve 13 by configuring the attachment mechanism 108 in such a manner that it facilitates capture by the advancing inner member 15. In such an embodiment, adding stiffness to, and/or gathering up the sleeve over several millimeter or centimeters (such as using a plurality of attachment bands 108) would improve the reliability of the sleeve 13 being effectively fed into the passageway 22 as the inner member 15 is advanced.

The eversible sleeve introducer 11 of the present invention can also be used to deliver stents 61 and other tubular prosthetic devices as depicted in FIGS. 20-21. In the embodiment of FIG. 20, a stent 61, such as a self-expanding intraluminal stent, is mounted over the inner member 15 and this assembly is loaded within the tubular introducer member 12. The sleeve 13 is everted into the passageway 22 of the inner member 15 which functions as the delivery or pusher catheter. The inner member 15 includes a lip 63 that maintains a force against the proximal end of the stent 61 that assists in placement of the stent 61 at the desired location. The stent 61 is advanced out of the introducer member 12 as the sleeve 13 is everted and subsequently protects the lining of the bodily passage from the friction that would result from the advancing stent 61. When the sleeve 13 has finished everting from the passageway, the stent 61 becomes exposed to the bodily passage into which it is to be placed. In the case of a self-expanding stent 61, the sleeve 13 may also provide a restraint that helps prevent its full expansion. As the sleeve 13 passes over and exposes the advancing stent, the deploying stent 61 is able to expand against the walls of the bodily passage. In a related embodiment shown in FIG. 21, the loaded stent 61 is made of a lower profile because it is not delivered from within the introducer member 12 which otherwise adds to the outer diameter of the introducer apparatus 10. In the illustrative embodiment, the distal end 16 of the introducer member 12 does not extend over any portion of the stent 61 which has been mounted over the inner member 15. The inner member 15 of this embodiment also includes a lip 63. Without the introducer member 12 extending over the stent 61, the sleeve 13 provides the only restraint and protection to the stent as it is delivered. In this particular embodiment, the stent 61 is sized to include a space 86 between the inside of the stent 61 and the outer surface of the inner member 15. The space 86 permits the inner member 15 to be readily withdrawn from within the passageway 87 of the stent 61 without catching thereon and possibly causing it to be dislodged from the target area of deployment. Alternatively, the stent could be mounted on a balloon and deployed in that manner once exposed by everted sleeve and/or introducer member.

FIG. 22 depicts an embodiment in which a series of friction reduction means 68 are included about the distal tip 29 of an inner member 15 of an introducer apparatus 10. In the illustrative embodiment, the friction reduction means 68 includes three ball bearings 88 or beads which a mounted in the distal face 67 of the distal tip 29. The ball bearings 88 are rotatable within their mountings via friction applied by the sleeve 13 as it drags thereover, therefore allowing the sleeve 13 to move more freely. A similar concept is shown in FIG. 22A wherein a series of rollers 89 are mounted about the distal face, encircling the passageway 22 opening. In the illustrative embodiment, the hollow rollers 89 are threaded over a wire frame 90 which comprises two opposing semi-circular frame halves 124, 125. The adjacent first ends 91 of the two wire frame halves 124, 125 are embedded into the distal face 67 at a point along passageway 22 opening and the seconds ends 123 are embedded into the distal face 67 approximately 180° from the first ends 91 along the passageway 22 opening, such that the wire frame 90 is circular with each frame half 124, 125 holding approximately half of the rollers 89. Optional supports 122 mounted on the distal face 67 support the wire frame 90 and provide spacers between the rollers 89. Other means of reducing friction include providing a highly lubricious material to the distal face 67 (e.g., a highly polished metal tip annular ring), coating the end of the device with lubricious polymer coating such as SLIP-COAT® (Sterilization Technical Services, Rush, N.Y.), or changing the surface energy of the distal face 67 through other means such as ion beam bombardment.

Figure 25:
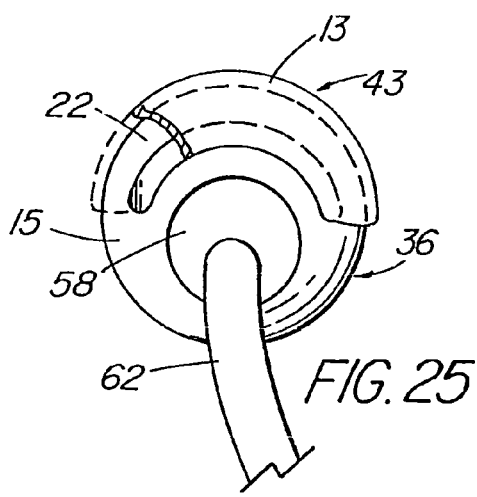
FIG. 25 depicts an end view of an embodiment of the present invention having a dual lumen introducer.
Figure 26:
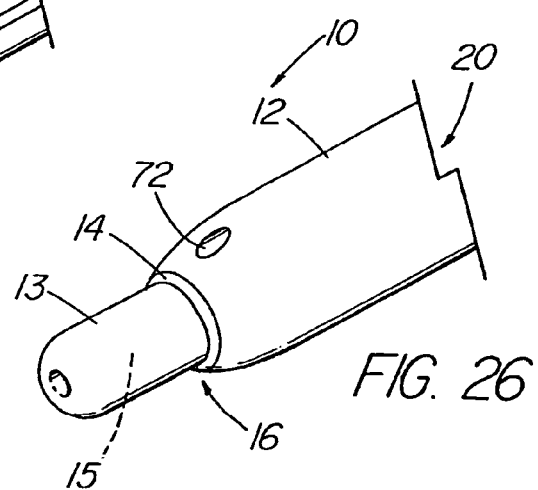

While the embodiments of the preceding figures generally provide for a single passageway 22 through which materials or devices can be introduced to the target site, it possible to provide for one or more additional lumens in the introducer apparatus 10 separate from the passageway 22 that houses the eversible sleeve 13. As depicted in FIG. 25, the inner member 15 includes a second passageway 58 for passage of a device, such as a wire guide 62, or for injection of contrast media or other materials. In this embodiment, the sleeve 13 represents a partial sleeve 43. The partial sleeve 43 allows the second passageway 58 to remain continually open and accessible at all times, while still providing a degree of friction reduction between a portion of the inner member 15 and the bodily passage. FIGS. 26-27 show embodiments in which the introducer member 12 includes a second passageway 72. In the embodiment of FIG. 26, the sleeve 13 and the attachment means 14 to the introducer member 12 are similar to single passageway embodiments such as that of FIG. 1. The second passageway 72, located proximal to the sleeve attachment 14, is especially useful as an injection port, but can also function to receive a wire guide, if appropriately sized. A second multi-lumen introducer member 12 is depicted in FIG. 27 wherein the distal end 16 of the introducer member is more truncate than that of FIG. 26 and the sleeve attachment 14 comprises an annular or ring structure mounted on the distal end 16 with the opening to the second passageway 72 being positioned on the face of the distal end 16 adjacent to the sleeve 13 and attachment 14. The attachment 14 can either be a plastic or metal ring to secure the sleeve 13 to the introducer member 12, or a ring of adhesive. As mentioned, the embodiment of FIG. 27 also includes a longitudinal opening 74 to allow the introducer member 12 to be removed from over the inner member 15 with the sleeve 13 and attachment 14 made splittable or detachable as well to allow removal over the inner member 15. Obviously, it is possible to have additional passageways beyond the second passageway 58, 72 depicted in FIGS. 25-27. For example the second passageway 58, 72 might be used for introduction of wire guides or medical devices while the third passageway is used for injecting contrast media.

Figure 28:
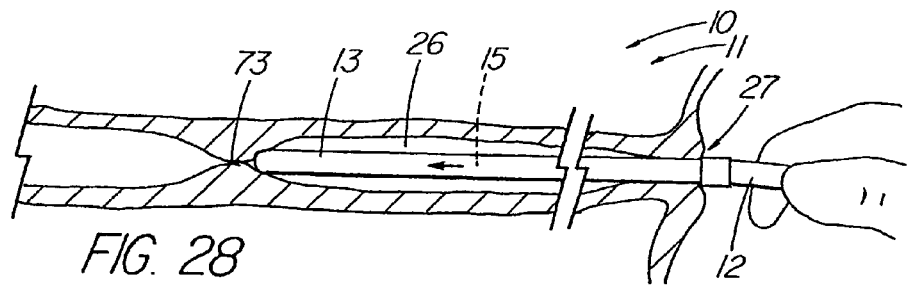
FIGS. 28-30 depict an embodiment of the present invention being used with a bodily passage.
Figure 29:
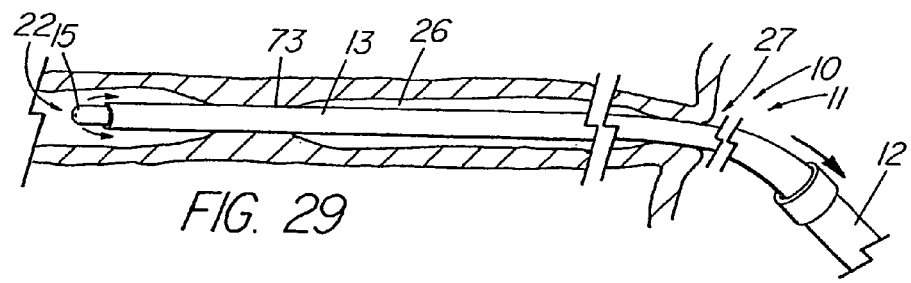
Figure 30:
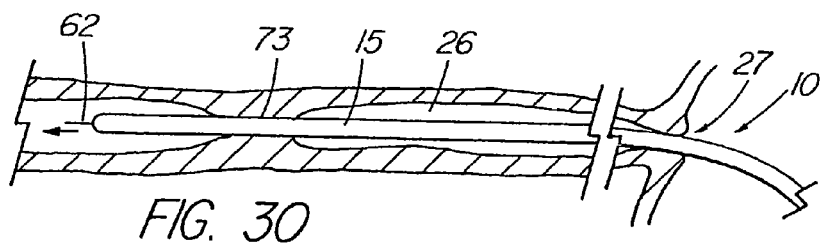

FIGS. 28-30 depict an example of a method of using a selected embodiment of the present invention to cannulate a stricture within a bodily passage. As depicted in FIG. 28, the distal end 16 of the introducer member 12 is placed against the opening 27 to the bodily passage 26 where the introducer member 12 is then pulled back relative the inner member 15 which is initially restrained. This allows the inner member 15 to grip the opening and -advance into bodily passage 26 as the sleeve 13 is laid down when everting from the inner member 15. In FIG. 29, the inner member 15 has passed through the stricture and the sleeve 13 has now completely everted from the passageway 22 of the inner member. The inner member 15 is maintained at the target site, while the introducer assembly 11 is removed from the patient by one of several mean discussed above. In FIG. 30, only the inner member 15 remains from the original introducer apparatus 10. It can serve as an introducer for a wire guide 62 or other medical treatment device and may be itself removed from the patient once access across the stricture is gained, leaving the wire guide and/or other device(s) in place. It should be noted that unlike procedures such as nasal, colonic, and urethral access where it is advantageous or desired to improve patient comfort during both ingress and egress of the introducer apparatus 10, it may be less important in other medical procedures, such as cannulation of certain internal sphincters and strictures, to maintain the sleeve 13 in place during removal of the inner member 15, the critical function of the sleeve 13 having been already fulfilled.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

What is claimed is:

1. An introducer apparatus for providing a reduced-friction pathway through an internal bodily passage of a patient, comprising:
a flexible introducer member having a distal end and a proximal end, the introducer member being adapted to be introduced into the patient through an endoscope;
a sleeve comprising a flexible material and which includes a first end, a second end, a first body portion, and a second body portion, the first body portion being attached to the introducer member, the second body portion, which includes the second end, being moveable in response to movement of a second member sized for introduction through the introducer member and through the internal bodily passage;
whereby the second body portion, including the second end, is disposed within and is eversible from a passageway of the second member such that the second member passageway is substantially unobstructed upon full deployment of the second member; and
whereby the sleeve provides a reduced-friction pathway for at least a portion of the second member during advancement thereof through the internal bodily passage.

2. The apparatus of claim 1, wherein the sleeve is an elongate tubular member having a passageway therethrough.

3. The apparatus of claim 2, wherein the sleeve comprises a thin polymeric film.

4. The apparatus of claim 3, wherein the sleeve comprises expanded polytetrafluoroethylene.

5. The apparatus of claim 3, wherein the sleeve comprises polyethylene.

6. The apparatus of claim 2, wherein the sleeve includes a plurality of apertures disposed thereabout.

7. The apparatus of claim 2, wherein the sleeve is configured to bias the second member in a predetermined direction in at least partial response to forward advancement of the second member within the sleeve.

8. The apparatus of claim 1, wherein the sleeve includes a circumferentially open portion extending at least partially along the length thereof.

9. The apparatus of claim 8, wherein the sleeve is non-tubular in shape, such that it extends only partially around the circumference of the introducer member to which it is attached.

10. The apparatus of claim 1, wherein at least a portion of the second member is disposed within the introducer member, further wherein the second member comprises an elongate tube.

11. The apparatus of claim 1, wherein the introducer member comprises an elongate tube.

12. The apparatus of claim 11 wherein the internal passage is the patient's duodenum, and wherein the elongate tube has a first end, a second end, and a length that is sufficient to permit the first end to be located adjacent to the patient's duodenum while the second end is located outside of the patient.

13. The apparatus of claim 11, wherein the elongate tube includes at least a second passageway extending therethrough.

14. The apparatus of claim 11, wherein the introducer member includes at least one longitudinal predetermined split line that permits, with manipulation by the operator, external access to the passageway of the introducer member to permit removal of the second member therefrom.

15. The apparatus of claim 1, wherein the introducer member comprises a plurality of longitudinal members that are configured to cooperate with the second member such that they are slidable relative to the second member to evert the sleeve from the passageway thereof.

16. The apparatus of claim 1, wherein the sleeve further includes a tether attached about the second end thereof, the tether sized such that the operator can reload the sleeve back into the second member from the proximal end of the introducer member.

17. The apparatus of claim 1, wherein the first end of the sleeve is permanently and circumferentially attached about an exterior surface of the introducer member.

18. The apparatus of claim 1, wherein the first end of the sleeve is releasably attached about the introducer member.

19. The apparatus of claim 1, wherein the second end of the sleeve is loadable into the passageway of the second member.

20. The apparatus of claim 1, wherein the sleeve further comprises a series of pleats, the pleats adapted to unfold longitudinally as the sleeve everts from the passageway of the inner member.

21. The apparatus of claim 1, wherein the introducer member includes a second passageway therein.

22. The apparatus of claim 1 further comprising an endoscope, wherein the endoscope comprises a distal end, a proximal end, and a working channel, and further wherein at least a portion of the introducer member is disposed within the working channel of the endoscope.

23. An introducer apparatus for providing a reduced-friction pathway through an internal bodily passage of a patient, comprising:
   a flexible introducer member having a distal end, a proximal end, and a passageway extending therethrough, the introducer member being adapted to be introduced into the patient through an endoscope;
   a second member having a distal end and a proximal end, the second member being slidably disposed within the passageway of the introducer member;
   a sleeve comprising a flexible material and which includes a first body portion having a first end, and a second body portion having a second end, the first end of the first body portion being attached to the introducer member, the second end and at least a portion of the second body portion being removably disposed within the passageway of the second member;
   whereby the second body portion is eversible from the passageway of the second member in response to movement of the second member relative to the introducer member, such that the passageway is substantially unobstructed by the sleeve upon full deployment of the second member;
   whereby a distal end of the second member is spaced distally apart from the second end of the sleeve upon full deployment of the second member; and
   whereby the sleeve provides a reduced-friction pathway for at least a portion of the second member during advancement thereof through the internal bodily passage.

24. The apparatus of claim 23, wherein the sleeve is at least 6 cm in length.

25. The apparatus of claim 23, wherein the sleeve is at least 20 cm in length and the introducer member comprises a feeding tube.

26. The apparatus of claim 23, wherein the introducer member and the second member each comprise elongate tubes.

27. The apparatus of claim 23, wherein the introducer member and second member each comprise catheters having a length of at least 150 cm.

28. The apparatus of claim 23, wherein the introducer member includes a second passageway, the second passageway being located relative to the point of attachment such that second passageway is not obstructed by a portion of the sleeve during use of the apparatus.

29. The apparatus of claim 23, wherein the distal end of the second member includes a friction-reducing mechanism located thereabout to facilitate passage of the sleeve thereover.

30. The apparatus of claim 23, wherein the second member is configured so as to be biased in a predetermined direction upon forward advancement within the sleeve.

31. The apparatus of claim 30, wherein the distal end of the second member is asymmetrical in shape.

32. The apparatus of claim 23, wherein the second member is adapted for delivery of a stent.

33. The apparatus of claim 23, wherein the apparatus is adapted for the introduction of a third member upon deployment of the second member.

34. The apparatus of claim 33, wherein the third member is preloaded within the passageway of the second member, the proximal end of the second member being configured to receive at least a portion of the third member.

35. The apparatus of claim 23, wherein the second member includes an expandable zone extending longitudinally therealong such that the passageway of the second member can be expanded in diameter.

36. The apparatus of claim 23, wherein the introducer member comprises a plurality of longitudinal attachment strips adapted for attaching the sleeve to the introducer member, one or more of the plurality of longitudinal attachment strips being slidably disposed within channels formed in the introducer member.

37. The apparatus of claim 23, wherein the second end of the sleeve is attached to the second member.

38. The apparatus of claim 23, wherein the second member includes a fluid reservoir portion adapted for the delivery of fluids therefrom.

39. The apparatus of claim 23, wherein the endoscope comprises a distal end, a proximal end, and a working channel, and further wherein at least a portion of the introducer member is disposed within the working channel of the endoscope.

40. An introducer apparatus for providing a reduced-friction pathway into an internal bodily passage of a patient, comprising:
   a flexible introducer member having a distal end and a proximal end, the introducer member comprising an elongate tube adapted to be introduced into the patient through an endoscope;
   a sleeve comprising a flexible material and which includes a first body portion and a second body portion, the first body portion being attached to the introducer member, the second body portion being moveable in response to movement of a second member through the introducer member and into the internal bodily passage, the second member comprising an elongate tube adapted to slide through an internal passageway of the introducer member;
   whereby the second body portion is unattached to the second member and is disposed within and eversible from a passageway thereof, such that the second member passageway, upon full deployment of the second member, is unobstructed by the sleeve; and
   whereby the sleeve provides a reduced-friction pathway for at least a portion of the second member during advancement of the second member into the bodily passage.

41. An introducer apparatus for providing a reduced-friction pathway into an internal bodily passage of a patient, comprising:
   a flexible introducer member comprising an elongate tubular member having an outer surface, a distal end, a proximal end, and a passageway extending therethrough, the introducer member being adapted to be introduced into the patient through an endoscopic device;
   a second member comprising an elongate tubular member having a distal end, the second member slidably disposed within the passageway of the introducer member;
   a tubular sleeve comprising a thin polymeric film and which includes a first body portion and a second body portion, the first body portion being attached about the outer surface of the introducer member at a location near the distal end of the introducer member, the second body portion comprising a second end that is removably disposed within the passageway of the second member, the sleeve being responsive to movement of the second member as the distal end of the second member advances relative to and beyond the distal end of the introducer member; and whereby the second end of the second body portion is completely eversible from the second member passageway, thereby providing a reduced-friction pathway for at least a portion of the second member, as the distal end of the second member is advanced into the internal bodily passage and distally beyond the second end of the second body portion of the sleeve.

* * * * *